(12) United States Patent
Borysyuk et al.

(10) Patent No.: US 9,745,592 B2
(45) Date of Patent: Aug. 29, 2017

(54) ENGINEERED PLANT BIOMASS FOR BIODIESEL AND BIOETHANOL PRODUCTION

(75) Inventors: Mykola Borysyuk, Somerset, NJ (US); Natalia Pogrebnyak, Highland Park, NJ (US); Vyacheslav Andrianov, Warrington, PA (US); Igor Kostenyuk, Danville, VA (US)

(73) Assignee: Tyton Biosciences, LLC, Danville, VA (US)

( * ) Notice: Subject to any disclaimer, the term of this patent is extended or adjusted under 35 U.S.C. 154(b) by 263 days.

(21) Appl. No.: 14/241,733

(22) PCT Filed: Aug. 30, 2012

(86) PCT No.: PCT/US2012/053099
§ 371 (c)(1),
(2), (4) Date: Oct. 21, 2014

(87) PCT Pub. No.: WO2013/033369
PCT Pub. Date: Mar. 7, 2013

(65) Prior Publication Data
US 2015/0211015 A1    Jul. 30, 2015

Related U.S. Application Data

(60) Provisional application No. 61/529,532, filed on Aug. 31, 2011.

(51) Int. Cl.
| | |
|---|---|
| *C12N 15/82* | (2006.01) |
| *C12N 15/62* | (2006.01) |
| *C12N 9/90* | (2006.01) |
| *C10L 1/02* | (2006.01) |
| *C12N 5/04* | (2006.01) |
| *C12N 9/28* | (2006.01) |
| *C12N 9/30* | (2006.01) |

(52) U.S. Cl.
CPC .......... *C12N 15/8245* (2013.01); *C10L 1/026* (2013.01); *C12N 5/04* (2013.01); *C12N 9/242* (2013.01); *C12N 9/2417* (2013.01); *C12N 9/90* (2013.01); *C12N 15/62* (2013.01); *C12N 15/8201* (2013.01); *C12N 15/8247* (2013.01); *C10L 2200/0476* (2013.01); *C10L 2270/026* (2013.01); *C12Y 504/00* (2013.01)

(58) Field of Classification Search
None
See application file for complete search history.

(56) References Cited

U.S. PATENT DOCUMENTS

| | | | | |
|---|---|---|---|---|
| 6,096,546 | A * | 8/2000 | Raskin | C07K 14/005 210/600 |
| 7,572,950 | B2 * | 8/2009 | Herbers | C12N 9/90 435/320.1 |
| 7,655,836 | B2 * | 2/2010 | Birch | C12N 9/90 435/100 |
| 2009/0265810 | A1 | 10/2009 | Andre et al. | |
| 2011/0201059 | A1 | 8/2011 | Hall et al. | |
| 2011/0207181 | A1 | 8/2011 | Birch et al. | |

FOREIGN PATENT DOCUMENTS

| | | |
|---|---|---|
| CN | 102066567 A | 5/2011 |
| WO | 2009152285 A1 | 12/2009 |

OTHER PUBLICATIONS

Wu et al. Plant Biotechnology Journal 5: 109-117 (2007).*
Andrianov et al. Plant Biotechnology Journal 8(3): 277-287 (Apr. 2010).*
Wang et al. Indian Journal of Biochemistry and Biophysics 44: 26-30 (2007).*
International Search Report for PCT/US2012/053099 dated Mar. 11, 2013.

* cited by examiner

*Primary Examiner* — David T Fox
(74) *Attorney, Agent, or Firm* — NK Patent Law, PLLC

(57) ABSTRACT

The disclosure encompassed herein relates, in part, to a method for increasing energy density of plant biomass that can be used for production of renewable fuel, such as biodiesel oil and/or ethanol. In an aspect, genetic engineering for enhanced sugar accumulation can be achieved by overexpressing a bacterial enzyme sucrose isomerase. Sugars or oils extracted from the plants of the disclosure encompassed herein may be used for industrial purposes such as heating, producing bio-fuels such as biodiesel fuel, or lubricating applications.

41 Claims, 7 Drawing Sheets

Figure 1A

SEQ ID NO: 6

Codon-optimized sucrose-isomerase (palatinose) gene sequence with signal peptides

```
ATGGCAACACAGAGGAGGGCTAACCCTTCATCATTACATTTGATTACAGTTTTCAGTTTA      60
TACCGTTGTGTCTCCTCCCGATTGGGAAGTAGTAATGTAAACTAATGTCAAAAGTCAAAT
 M  A  T  Q  R  R  A  N  P  S  S  L  H  L  I  T  V  F  S  L
*Calreticulin SP CTTGTGGCAGTGGTTTCTGCTAGCAGATTCAATCCAATTAGACTCCCAACAACACATGAA     120
GAACACCGTCACCAAAGACGATCGTCTAAGTTAGGTTAATCTGAGGGTTGTTGTGTACTT
 L  V  A  V  V  S  A  S  R  F  N  P  I  R  L  P  T  T  H  E
                         Sporamin vacuolar propeptide CCTGCTCCTTCATTAACTGTGCAACAGAGTAATGCATTGCCTACTTGGTGGAAACAGGCA     180
GGACGAGGAAGTAATTGACACGTTGTCTCATTACGTAACGGATGAACCACCTTTGTCCGT
 P  A  P  S  L  T  V  Q  Q  S  N  A  L  P  T  W  K  Q  A
       Mature Protein GTGTTTTATCAGGTGTATCCTAGAAGTTTTAAAGATACAAATGGTGATGGAATTGGTGAT     240
CACAAAATAGTCCACATAGGATCTTCAAAATTTCTATGTTTACCACTACCTTAACCACTA
 V  F  Y  Q  V  Y  P  R  S  F  K  D  T  N  G  D  G  I  G  D TTGAACGGTATTATTGAAAACCTTGATTATCTTAAAAAACTTGGAATTGATGCTATTTGG     300
AACTTGCCATAATAACTTTTGGAACTAATAGAATTTTTTGAACCTTAACTACGATAAACC
 L  N  G  I  I  E  N  L  D  Y  L  K  K  L  G  I  D  A  I  W ATTAACCCACACTATGATTCTCCAAATACTGATAATGGTTATGATATTAGAGATTATAGA     360
TAATTGGGTGTGATACTAAGAGGTTTATGACTATTACCAATACTATAATCTCTAATATCT
 I  N  P  H  Y  D  S  P  N  T  D  N  G  Y  D  I  R  D  Y  R AAGATTATGAAAGAATATGGTACTATGGAGGATTTTGATAGACTTATTTCTGAAATGAAG     420
TTCTAATACTTTCTTATACCATGATACCTCCTAAAACTATCTGAATAAAGACTTTACTTC
 K  I  M  K  E  Y  G  T  M  E  D  F  D  R  L  I  S  E  M  K AAGAGGAACATGAGGCTTATGATTGATATTGTTATTAATCACACATCAGATCAACATGCA     480
TTCTCCTTGTACTCCGAATACTAACTATAACAATAATTAGTGTGTAGTCTAGTTGTACGT
 K  R  N  M  R  L  M  I  D  I  V  I  N  H  T  S  D  Q  H  A TGGTTCGTGCAGTCAAAGTCTGGAAAAAAACAATCCATACAGAGATTACTACTTTTGGAGG     540
ACCAAGCACGTCAGTTTCAGACCTTTTTTGTTAGGTATGTCTCTAATGATGAAAACCTCC
 W  F  V  Q  S  K  S  G  K  N  N  P  Y  R  D  Y  Y  F  W  R GATGGTAAAGATGGTCATGCTCCTAATAATTATCCAAGTTTCTTTGGTGGTTCTGCATGG     600
CTACCATTTCTACCAGTACGAGGATTATTAATAGGTTCAAAGAAACCACCAAGACGTACC
 D  G  K  D  G  H  A  P  N  N  Y  P  S  F  F  G  G  S  A  W GAAAAAGATGATAAATCAGGACAATATTACTTGCATTATTTTGCTAAGCAACAACCAGAT     660
CTTTTTCTACTATTTAGTCCTGTTATAATGAACGTAATAAAACGATTCGTTGTTGGTCTA
 E  K  D  D  K  S  G  Q  Y  Y  L  H  Y  F  A  K  Q  Q  P  D
```

Figure 1B

SEQ ID NO: 7

```
TTAAATTGGGATAATCCAAAGGTTAGACAGGATCTTTACGATATGTTGAGATTTTGGTTG      720
AATTTAACCCTATTAGGTTTCCAATCTGTCCTAGAAATGCTATACAACTCTAAAACCAAC
 L   N   W   D   N   P   K   V   R   Q   D   L   Y   D   M   L   R   F   W   L

GATAAAGGTGTTTCTGGTTTAAGATTTGATACAGTTGCAACTTATAGTAAAATTCCAAAT      780
CTATTTCCACAAAGACCAAATTCTAAACTATGTCAACGTTGAATATCATTTTAAGGTTTA
 D   K   G   V   S   G   L   R   F   D   T   V   A   T   Y   S   K   I   P   N

TTTCCTGATCTCTCTCAACAACAGCTTAAAAACTTCGCTGAGGAATATACAAAGGGTCCA      840
AAAGGACTAGAGAGAGTTGTTGTCGAATTTTTGAAGCGACTCCTTATATGTTTCCCAGGT
 F   P   D   L   S   Q   Q   Q   L   K   N   F   A   E   E   Y   T   K   G   P

AAAATTCACGATTATGTTAATGAAATGAACAGAGAGGTGCTTTCTCATTACGATATTGCT      900
TTTTAAGTGCTAATACAATTACTTTACTTGTCTCTCCACGAAAGAGTAATGCTATAACGA
 K   I   H   D   Y   V   N   E   M   N   R   E   V   L   S   H   Y   D   I   A

ACAGCTGGTGAAATTTTCGGAGTTCCACTTGATAAATCAATTAAGTTTTTCGATAGAAGA      960
TGTCGACCACTTTAAAAGCCTCAAGGTGAACTATTTAGTTAATTCAAAAAGCTATCTTCT
 T   A   G   E   I   F   G   V   P   L   D   K   S   I   K   F   F   D   R   R

AGAAATGAATTGAATATTGCATTTACTTTCGATCTCATTAGATTGGATAGAGATGCAGAT     1020
TCTTTACTTAACTTATAACGTAAATGAAAGCTAGAGTAATCTAACCTATCTCTACGTCTA
 R   N   E   L   N   I   A   F   T   F   D   L   I   R   L   D   R   D   A   D

GAAAGATGGAGAAGGAAGGATTGGACTTTAAGTCAATTCAGAAAAATTGTTGATAAGGTT     1080
CTTTCTACCTCTTCCTTCCTAACCTGAAATTCAGTTAAGTCTTTTTAACAACTATTCCAA
 E   R   W   R   R   K   D   W   T   L   S   Q   F   R   K   I   V   D   K   V

GATCAAACAGCAGGAGAGTACGGATGGAATGCTTTCTTTCTCGATAATCATGATAACCCA     1140
CTAGTTTGTCGTCCTCTCATGCCTACCTTACGAAAGAAAGAGCTATTAGTACTATTGGGT
 D   Q   T   A   G   E   Y   G   W   N   A   F   F   L   D   N   H   D   N   P

AGGGCTGTTTCACATTTTGGAGATGATAGGCCACAGTGGAGGGAGCATGCTGCAAAGGCT     1200
TCCCGACAAAGTGTAAAACCTCTACTATCCGGTGTCACCTCCCTCGTACGACGTTTCCGA
 R   A   V   S   H   F   G   D   D   R   P   Q   W   R   E   H   A   A   K   A

TTGGCAACTCTTACTCTCACTCAGAGAGCAACTCCATTTATTTACCAGGGATCTGAGTTA     1260
AACCGTTGAGAATGAGAGTGAGTCTCTCGTTGAGGTAAATAAATGGTCCCTAGACTCAAT
 L   A   T   L   T   L   T   Q   R   A   T   P   F   I   Y   Q   G   S   E   L

GGTATGACTAACTACCCTTTTAAGAAGATTGATGATTTCGATGATGTGGAAGTGAAGGGA     1320
CCATACTGATTGATGGGAAAATTCTTCTAACTACTAAAGCTACTACACCTTCACTTCCCT
 G   M   T   N   Y   P   F   K   K   I   D   D   F   D   D   V   E   V   K   G

TTTTGGCAAGATTATGTTGAAACAGGTAAGGTTAAAGCTGAAGAATTTCTCCAGAACGTT     1380
AAAACCGTTCTAATACAACTTTGTCCATTCCAATTTCGACTTCTTAAAGAGGTCTTGCAA
 F   W   Q   D   Y   V   E   T   G   K   V   K   A   E   E   F   L   Q   N   V

AGACAAACTTCAAGGGATAATTCAAGGACACCTTTCCAGTGGGATGCATCAAAAAATGCT     1440
TCTGTTTGAAGTTCCCTATTAAGTTCCTGTGGAAAGGTCACCCTACGTAGTTTTTTACGA
 R   Q   T   S   R   D   N   S   R   T   P   F   Q   W   D   A   S   K   N   A
```

Figure 1C

SEQ ID NO: 8

```
GGATTTACTTCAGGAACACCATGGCTCAAAATTAACCCAAATTACAAGGAGATTAATTCT    1500
CCTAAATGAAGTCCTTGTGGTACCGAGTTTTAATTGGGTTTAATGTTCCTCTAATTAAGA
 G  F  T  S  G  T  P  W  L  K  I  N  P  N  Y  K  E  I  N  S

GCTGATCAGATTAATAATCCTAACAGTGTGTTTAATTATTACAGAAAGCTTATTAATATT    1560
CGACTAGTCTAATTATTAGGATTGTCACACAAATTAATAATGTCTTTCGAATAATTATAA
 A  D  Q  I  N  N  P  N  S  V  F  N  Y  Y  R  K  L  I  N  I

AGGCATGATATTCCTGCTTTGACTTACGGAAGTTATATTGATCTTGATCCAGATAATAAT    1620
TCCGTACTATAAGGACGAAACTGAATGCCTTCAATATAACTAGAACTAGGTCTATTATTA
 R  H  D  I  P  A  L  T  Y  G  S  Y  I  D  L  D  P  D  N  N

TCAGTTTATGCATATACAAGGACTCTTGGAGCAGAAAAATATCTCGTTGTGATTAACTTT    1680
AGTCAAATACGTATATGTTCCTGAGAACCTCGTCTTTTTATAGAGCAACACTAATTGAAA
 S  V  Y  A  Y  T  R  T  L  G  A  E  K  Y  L  V  V  I  N  F

AAAGAAGAAGTTATGCATTATACATTGCCTGGAGATTTGAGTATTAATAAAGTTATTACA    1740
TTTCTTCTTCAATACGTAATATGTAACGGACCTCTAAACTCATAATTATTTCAATAATGT
 K  E  E  V  M  H  Y  T  L  P  G  D  L  S  I  N  K  V  I  T

GAAAATAATTCTCACACTATTGTTAACAAGAATGATAGACAATTGAGGCTTGAACCATGG    1800
CTTTTATTAAGAGTGTGATAACAATTGTTCTTACTATCTGTTAACTCCGAACTTGGTACC
 E  N  N  S  H  T  I  V  N  K  N  D  R  Q  L  R  L  E  P  W

CAAAGTGGAATTTACAAGCTCAATCCTTGAGGAGAGCTCAGTCGAC    1846
GTTTCACCTTAAATGTTCGAGTTAGGAACTCCTCTCGAGTCAGCTG
 Q  S  G  I  Y  K  L  N  P  *
```

Expression cassette for sucrose isomerase in vector pUC57

Car-sp: calreticulin signal peptide
Spo: sporamine vacuolar targeting signal

Transformation vectors for expression sucrose isomerase in plants

PCR analysis of introduced sucrose isomerase gene in transformed tobacco

Primers for plan PCR-analysis (10-24-08)

PalI-forI:
CTGCTAGCAGATTCAATCCAATTAGACTCCC

PalI-rev1:
TAAAGATCCTGTCTAACCTTTGGATTATCCC

Fragment size: 620 bp

Expression of bacterial sucrose isomerase leads to accumulation of palatinose

Palatinose in selected tobacco lines overexpressing PalI gene under the control of 35S promoter (S) and Rubisco promoter (R), as detected by GC-MS.

ENGINEERED PLANT BIOMASS FOR BIODIESEL AND BIOETHANOL PRODUCTION

CROSS-REFERENCE TO RELATED APPLICATIONS

The present application is a U.S. National Stage Entry of International Patent Application No. PCT/US2012/053099, filed 30 Aug. 2012, which in turn claims priority benefit from U.S. Provisional Patent Application No. 61/529,532, filed 31 Aug. 2011, all of which are hereby incorporated by reference in their entireties.

REFERENCE TO SEQUENCE LISTING

The sequence data in the ASCII text filed submitted via electronic filing system ("EFS") on Mar. 26, 2015, is incorporated herein by reference. The ACSII text file is named "010463-5001_Sequence_listing.txt", was created on Mar. 26, 2015, and is 16.461 kilobytes in size.

BACKGROUND

Growing demand for alternative sources of energy can be fulfilled at least in part with a renewable supply of plant-derived biofuel oil and/or ethanol. To be a viable alternative to fossil fuels, the biofuel should provide a net energy gain in production, have environmental benefits, be economically competitive, and producible in large quantities without reducing food supplies, a current unintended byproduct of existing biofuel production.

The two predominant U.S. alternative transportation fuels, relative to fossil gasoline and diesel, are ethanol fermented from corn grain starch and biodiesel oil extracted from soybean seeds. Both corn and soybean are staple crops, on which national food supply significantly relies. Corn ethanol yields 25% more energy than the energy invested in its production, whereas biodiesel yields 93% more. Relative to the fossil fuels they displace, greenhouse gas emissions are reduced 12% by the production and combustion of ethanol and 41% by biodiesel. Biodiesel also releases fewer air pollutants per net energy gain than ethanol. These advantages of biodiesel over ethanol come from lower agricultural inputs and more efficient conversion of feedstocks to fuel. However, according to a recent estimation by Hill et al. (Proc Natl Acad Sci USA. 2006, 103(30):11206-11210), even dedicating all U.S. corn and soybean production to biofuels would meet only 12% of the gasoline demand and 6% of the demand for diesel.

High biomass plants, particularly broad leaf high biomass plants, have great biofuel potential. Plants that can yield between 100-400 tons/acre of low-cost, high-value biomass materials are particularly useful especially when there are none of the high costs, labor requirements, chemical inputs, or geographic restrictions associated with low biomass plant production.

While large number of plants have been investigated as alternative energy resources, tobacco (*Nicotiana tabacum* and other species from the *Nicotiana* genus) has been mostly overlooked. Similar to hardwood trees, tobacco will coppice or re-sprout from its stump after it has been cut. Coppicing makes multiple harvests in a year possible, enabling it to produce very high biomass tonnage. Tobacco thrives on different kinds of soil in a wide range of environments. The yield of tobacco seeds amounts to 600 kg/ha. The oil content in tobacco seed ranges between 36% and 41% by weight (Giannelos P N, Zannikos S, Stournas S, Lois E, Anastoloulos G. Industrial Crops and Products 2002, 16:1-9), indicating the existence of potent oil synthesis machinery, comparable to one of the traditional oil producers, such as soybean or rapeseed. Recent experiments indicated that tobacco seed oil can partially substitute petroleum diesel fuel at most operating conditions in terms of performance parameters and emissions without any engine modification and preheating of the blends (Gunstone F. D., Pollard M., In F. D. Gunstone, ed, Structured and Modified Lipids. Marcel Dekker, New-York, pp 155-184 (2001); Usta N., Biomass and Bioenergy 2005, 28: 77-86).

Ideally, what is needed to support national alternative transportation fuel demands is biofuels produced from low-input biomass grown on agriculturally marginal land, using high-biomass plant species that are not involved in the food supply chain.

Plant lipids in the form of vegetable oil are a major plant product with great economic importance in human nutrition as well as a renewable feedstock for various industrial products and biofuels. Growing demand for alternative sources of energy can be fulfilled with a renewable supply of plant-derived fuel oil and/or ethanol. Plants represent a significant source of biofuel vegetable oil because many species accumulate oil lipids as major storage components in seeds. The main form of vegetative storage oil in seeds, which represent, depending on the species, 15-50% of seed weight, is triacylglycerol (TAG). Despite accumulation in seeds, primary oil synthesis occurs in chloroplasts of green photosynthetic tissues, with sugars as the primary precursor for fatty acid synthesis (Durret et al., 2008). However, the primary substrate for oil synthesis are the carbohydrates generated in green photosynthetic tissues (leaves and stems) that are subsequently metabolized in chloroplasts to produce free fatty acids and acetyl-CoA units, the basic building blocks for TAG. Therefore, plant leaves are the main place of building block synthesis for TAG, and as it has been experimentally examined, the amount of TAG accumulated in oil seeds may be in part determined by the amount of fatty acid produced in plastids. (Bao X, Ohlrogge J. Plant Physiol. 1999, 120:1057-62). Final storage of TAG occurs in seeds in small spherical organelles termed oil bodies (L. Planta, 1996, 208:503-511; Wahlroos T, Soukka J, Denesyuk A, Wahlroos R, Korpela T, Kilby N J. Genesis. 2003, 35(2): 125-132; Katavic V, Agrawal G K, Hajduch M, Harris S L, Thelen J J.; Proteomics. 2006, 16: 4586-4598). Only about 0.2-0.3% of leaf biomass is represented by TAG. Our recent metabolic engineering efforts [Andrianov et al., 2010] doubled the amount of extractable fatty acids from the green biomass (6% of dry weight) through of diacylglycerol acyltransferase (DGAT), a key enzyme in biosynthesis of the triacylglycerol (TAG) class of lipids [Jako C et al., 2001]. In addition, see U.S. Patent Application No. 2010/0184130 (Koprowski et al.), incorporated by reference. During the course of this study the inventors determined that doubling of lipid accumulation though overexpression of DGAT was accompanied by a decrease of the fatty acid precursor pool. In addition, the inventor's previous study with high-sugar variety of tobacco NC55 demonstrated that initial higher sugar content in plant tissue is favorable for higher accumulation of lipids. The inventors determined that the expression of rate-limiting factors, such as oil biosynthetis precursors, for example increasing the availability of sugars, a primary oil synthesis precursor, could correct the imbalance and support even greater synthesis and storage of TAG in green matter.

In a previously published study, Bornke et al (2002) have found that transgenic tobacco plant bearing isomaltulose synthase gene exhibited multiple severe phenotypic alterations: young leaves were curled and developed bleached areas during maturation, flowers were misshapen and sterile. In their experiments, isomaltulose was found in elevated concentrations in several subcellular compartments, coupled with general toxic effects (Bornke F, Hajrezaei M, Heineke D, Melzer M, Herbers K, Sonnewald U., Planta, 2002, 214, 3: 356-364.). It has also been shown that overexpression of the bacterial gene coding for sucrose isomerase, which transforms sucrose into isomaltulose, significantly increased total sugar amount in potato tubers (Boernke et al., 2002a), and doubled the total sugar content in sugarcane (Wu, Birch, 2007). However expression of this enzyme in cytosol of tobacco cells caused some morphological abnormalities in plant development (Boernke et al., 2002b).

BRIEF SUMMARY

The disclosure herein relates, in part, to a method for increasing energy density of plant biomass that can be used for production of renewable fuel, such as ethanol. The disclosure encompassed herein relates, in part, to the use of plants with enhanced sugar and oil (e.g., triacylglycerides) in its biomass that increase pool of metabolites for ethanol fermentation. In an embodiment, high-sugar plants could be naturally selected varieties or genetically engineered for higher sugar accumulation. Particularly, genetic engineering for enhanced sugar accumulation can be achieved, by, for example, overexpressing a bacterial enzyme sucrose isomerase (SI). The enhanced sugar is used as precursors for the fatty acids synthesis, which the basic component of vegetable oil. Increase in sugar concentration will significantly improve the efficiency of converting plant biomass into ethanol. Ethanol extracted from plants may be used for industrial purposes such as biofuel and important industrial ingredient.

The present disclosure provides, in part, an innovative metabolic engineering approach for further increasing the sugar content in plant biomass. Since sugar in plant biomass is the main compound that can be easily fermented to ethanol, in an embodiment, the disclosure herein encompasses increasing sugar concentration in order to improve the efficiency of converting plant biomass into ethanol. While the amount of sucrose that can be accumulated in plant tissues is under tight physiological control, some sucrose isomers, such as isomaltulose (also known as 6-O-alpha-D-glucopyranosyl-D-fructose and by the trade name PALATINOSE), can be accumulated to high concentrations in addition to sucrose.

In an embodiment, disclosed herein is a gene expression cassette which enhances content of biofuel synthesis precursors in plant biomass, as compared to unmodified plants, wherein the gene expression cassette comprises:
  a) at least one transcription regulating nucleotide sequence, wherein the transcription regulating nucleotide sequence is:
  i) a constitutive promoter;
  ii) an inducible promoter
  iii) a tissue-specific promoter
  iv) a developmentally regulated promoter
  v) a nucleotide sequence which is the complement or reverse complement of any of the previously mentioned nucleotide sequences under i) to iv), and functionally linked thereto; and
  vi) a combination thereof,
  b) at least one gene that enhances content of oil biofuel precursors in plant biomass, as compared to unmodified plants, selected from the group consisting of:
  i) a gene encoding SI;
  ii) the sequence as set forth in FIG. 1;
  iii) a gene encoding amylase;
  iv) a gene which suppresses starch synthesis; and
  v) combinations thereof.

In an embodiment, disclosed herein is a gene expression cassette wherein the chemically-inducible promoter is selected from a tetracycline-inducible promoter, an ethanol-inducible promoter, and a hormone-inducible promoter. In another embodiment, disclosed herein is gene expression cassette wherein the transcription regulating nucleotide sequence is a promoter selected from the group of CaMV 35S, Rubisco, a histone gene promoter, ubiquitin, criptic tCUP, VR-ACS1, CsVMV, ScBV, eLF4A-10, and ibAGP1. In another embodiment, disclosed herein is a gene expression cassette, wherein the gene expression cassette enhances sugar production of the plant biomass. In another embodiment, disclosed herein is a gene expression cassette, wherein the gene expression cassette enhances sugar content of the plant biomass. In another embodiment, disclosed herein is a gene expression cassette, wherein the gene expression cassette enhances sugar production and/or storage of the plant biomass, thereby enhancing biofuel content of the plant biomass. In another embodiment, disclosed herein is a gene expression cassette, wherein the gene expression cassette targets expression to plant vacuoles. In another embodiment, disclosed herein is a gene expression cassette, wherein the expression of said at least one sugar enhancing gene optionally coincides with the expression of introduced or native lipid biosynthesis genes. In another embodiment, disclosed herein is a gene expression cassette, further comprising at least one additional gene selected from the group consisting of an esterase, a thioesterase, lauryl-acyl carrier protein thioesterase, acyl CoA:diacylglycerol acyltransferase, Sn-2 acyltransferase, Lec2, oleosin, and combinations thereof. In another embodiment, disclosed herein is a gene expression cassette, wherein the concerted expression of sugar- and/or lipid-enhancing genes leads to elevated accumulation of fermented sugar and lipid in modified plant biomass compared to unmodified plants. In another embodiment, disclosed herein is a vector comprising the expression cassette.

In an embodiment, disclosed herein is a genetically modified plant with enhanced content of biofuel precursors in plant biomass, as compared to unmodified plants, wherein the gene expression cassette comprises:
  a) at least one transcription regulating nucleotide sequence, wherein the transcription regulating nucleotide sequence is:
  i) a constitutive promoter;
  ii) an inducible promoter
  iii) a tissue-specific promoter
  iv) a developmentally regulated promoter
  v) a nucleotide sequence which is the complement or reverse complement of any of the previously mentioned nucleotide sequences under i) to iv), and functionally linked thereto; and
  vi) a combination thereof,
  b) at least one gene that enhances content of oil biofuel precursors in plant biomass, as compared to unmodified plants, selected from the group consisting of:
  i) a gene encoding SI;
  ii) the sequence as set forth in FIG. 1;
  iii) a gene encoding amylase;
  iv) a gene which suppresses starch synthesis; and
  v) combinations thereof.

In an embodiment, disclosed herein is a genetically modified plant wherein said biosynthetic precursors are sugars. In an embodiment, disclosed herein is a genetically modified plant comprising at least one sugar- and/or lipid enhancing gene. In another embodiment, disclosed herein is a genetically modified plant comprising at least one sugar enhancing gene. In another embodiment, disclosed herein is a genetically modified plant wherein expression of sugar enhancing genes optionally coincides with the expression of introduced or native lipid biosynthetic genes. In another embodiment, disclosed herein is a genetically modified plant wherein the expression of sugar- and lipid-enhancing genes leads to elevated accumulation of fermented sugar and/or lipid in modified plant biomass compared to unmodified plants. In another embodiment, disclosed herein is a genetically modified plant which is used as a feedstock for simultaneous or sequential production of ethanol and/or biodiesel fuels. In another embodiment, disclosed herein is a genetically modified plant which is engineered by over-expressing sugar synthesis enzymes such as bacterial SI, starch degrading enzymes such as amylase that leads to sugar accumulation or by suppressing starch synthesis. In another embodiment, disclosed herein is a genetically modified plant wherein the metabolic flow is altered as compared to unmodified plants, resulting in the accumulation of higher yield of sugar and/or lipid.

In an embodiment, disclosed herein is a transgenic plant product, propagation material, cells, organs, parts, calli, cell cultures, seeds of transgenic progeny of the genetically modified plant. In another embodiment, disclosed herein is a genetically modified plant wherein said genetically modified plant is selected from the group of monocots, dicots, tobacco, maize, pea, canola, Indian mustard, millet, sunflower, hemp, switchgrass, duckweed, sugarcane, *sorghum*, and sugar beet. In another embodiment, disclosed herein is a genetically modified plant wherein said genetically modified plant is selected from the group of tobacco, hemp, switchgrass, and duckweed.

In an embodiment, disclosed herein is a genetically modified plant having an increased amount of sugar as compared to a non-genetically modified plant, and wherein said genetically modified plant is genetically modified with the gene expression cassette. In another embodiment, disclosed herein is a genetically modified plant having an increased amount of oil as compared to a non-genetically modified plant, and wherein said genetically modified plant is genetically modified with the gene expression cassette.

In an embodiment, disclosed herein is a process of engineering high-oil plant biomass using genetically modified plants with elevated content of biofuel synthesis precursors, compared to unmodified plants, as a host plant for metabolic engineering of lipids, comprising: a) introducing into the plant the gene expression cassette; and b) selecting transgenic plants with elevated content of oil biofuel precursors.

In an embodiment, disclosed herein is a process of producing a genetically modified plant with enhanced energy content as, wherein the method comprises the steps of: a) introducing into the plant the gene expression cassette; and b) selecting transgenic plants with enhanced energy content.

In an embodiment, disclosed herein is a process of producing a genetically modified plant with enhanced sugar content as compared to a corresponding control plant, wherein the method comprises the steps of: a) introducing into the plant the gene expression cassette; and b) selecting transgenic plants with enhanced sugar content. In another embodiment, disclosed herein is a process wherein said biosynthetic precursors are sugars. In another embodiment, disclosed herein is a process wherein said expression of sugar enhancing genes optionally coincides with the expression of introduced or native lipid biosynthesis genes. In another embodiment, disclosed herein is a process wherein the concerted expression of sugar- and/or lipid-enhancing genes leads to elevated accumulation of fermented sugar and lipid in modified plant biomass compared to unmodified plants. In another embodiment, disclosed herein is a process wherein the gene expression cassette enhances sugar content of the plant biomass. The disclosure encompassed herein further provides the process wherein the gene expression cassette enhances sugar production of the plant biomass, thereby enhancing oil content of the plant biomass. In another embodiment, disclosed herein is a process wherein the gene expression cassette targets expression to plant vacuoles. In another embodiment, disclosed herein is a process wherein the genetically modified plant is selected from the group of monocots, dicots, tobacco, maize, pea, canola, Indian mustard, millet, sunflower, hemp, switchgrass, duckweed, sugarcane, *sorghum*, and sugar beet. In another embodiment, disclosed herein is a process wherein the biomass of the genetically modified plant is used for the production of both biodiesel and bioethanol.

In an embodiment, disclosed herein is a process of producing bioethanol comprising: providing genetically modified plant biomass comprising the gene expression cassette; converting the plant biomass to bioethanol. In another embodiment, disclosed herein is a process wherein said genetically modified plant biomass is selected from the group of monocots, dicots, tobacco, maize, pea, canola, Indian mustard, millet, sunflower, hemp, switchgrass, duckweed, sugarcane, *sorghum*, and sugar beet.

BRIEF DESCRIPTION OF SEVERAL VIEWS OF THE DRAWINGS

The disclosure herein is described in conjunction with the following drawings in which like reference numerals designate like elements and wherein:

FIG. 1 depicts the sequence of a codon-optimized sucrose-isomerase (isomaltulose) gene sequence with signal peptides. FIGS. 1A to 1C show the nucleotide sequence for the sucrose-isomerase (isomaltulose) gene.

Figure 2:
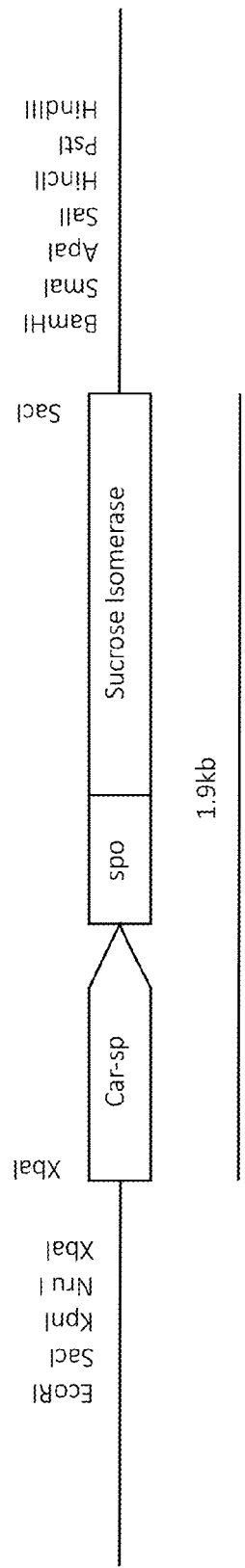
FIG. 2 depicts an expression cassette for SI in vector pUC57. Car-sp is the calreticulin signal peptide and Spo is the sporamin vacuolar targeting signal.
Figure 3:
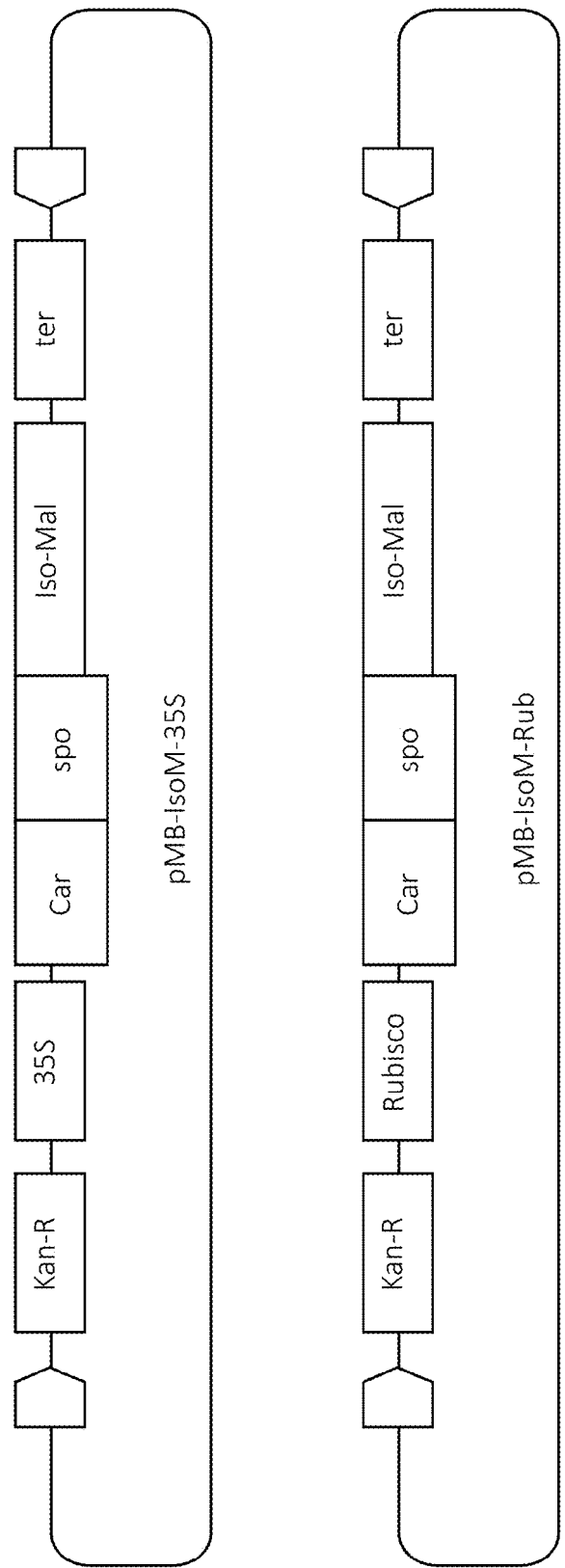
FIG. 3 depicts transformation vectors for expression SI in plants.

Tobacco plants that express vacuole-targeted SI did not show any visible morphological abnormalities.

DETAILED DESCRIPTION

Disclosed herein is a gene expression cassette comprising one or more genes, wherein the gene expression cassette can be used to specifically engineer a tobacco plant to increase the production of one or more metabolic products. In an embodiment, also disclosed herein, at least one of the peptides expressed from the gene expression cassette comprises a vacuolar targeting sequence. Also disclosed herein are genetically engineered tobacco plants for increased accumulation of sugars and fatty acids using a combination of several key genes at the same time. In one previous study, tobacco plants were created having double the amount of fatty acids (6% of dry weight) through overexpression under a strong RuBisCo promoter of diacylglycerol acyltransferase (DGAT), a key enzyme in biosynthesis of the triacylglycerol (TAG) class of lipids; and regulated expression of transcription factor LEC2 (Andrianov et al., 2009). Combining both traits in the same plant using genetic crossing or simultaneous transformation of two genes may result in a further increase of oil accumulation. From data obtained, it was clear that overexpression of these two genes is also accompanied by a decrease of the fatty acid precursors pool as well as increased levels of some phospholipids that are utilized in the oil body membranes. Therefore, in an embodiment, the expression of rate-limiting factors could correct the imbalance and support even greater synthesis and storage of TAG in green matter (Roesler et al., 1997). In an embodiment, a corresponding key enzyme of lipid metabolism Acetyl-CoA carboxylase (ACC) from *Arabidopsis* is overexpressed in tobacco under control of the strong 35S promoter and targeted to chloroplasts using corresponding signal peptides. This should provide a significant increase in the pool of precursors for fatty acid biosynthesis. In an embodiment, to generate an extended reservoir for TAG storage in leaf tissue a gene coding for the *Arabidopsis* oleosin protein (OLE1), which together with phospholipids forms the oil body membranes (Purkrtova et al., 2008), can be expressed in tobacco under the control a strong constitutive promoter. A combination of the DGAT and OLE1 genes will be transformed in the same plant generating a cumulative effect resulting in higher accumulation of TAGs in storage oil bodies. In addition, a previous study demonstrated that initial higher sugar content in plant tissue is favorable for higher accumulation of the precursors of the lipids. In an embodiment, the disclosure encompassed herein provides compositions and methods for increasing sugar content in plant tissue in order to accumulate precursors for lipid biosynthesis.

As noted elsewhere herein, Bornke et al (2002) have found that transgenic tobacco plant bearing isomaltulose synthase gene exhibited multiple severe phenotypic alterations. In their experiments, isomaltulose was not targeted into vacuole, instead it was found in elevated concentrations in several subcellular compartments, indicating general toxic effects if not properly directed. In an embodiment, to achieve a higher level of sugar accumulation in green biomass a bacterial enzyme, SI, that converts sucrose into its storage isomer isomaltulose (Wu L, Birch R G, 2007), can be expressed in tobacco under three different promoters (CaMV35S, RbcS, and WRKY53) with vacuolar-targeted signal, also referred to herein as a "vacuolar-targeting sequence". As described in greater detail herein, a vacuolar targeting sequence fused to a protein of interest enables the specific transport and localization of that fusion protein to a vacuole in a cell.

A "vacuolar-targeting sequence" can refer to a nucleic acid sequence or to an amino acid sequence, depending upon the context of the usage of the term. In an embodiment, a vacuolar-targeting amino acid sequence is the amino acid sequence encoded by a vacuolar-targeting nucleic acid sequence which, in some embodiments, is included in a gene expression cassette as disclosed herein.

Molecular mechanisms of processing vacuolar targeted proteins such as barley aleurain, lectin, sweet potato sporamin and tobacco chitinase A have been researched for more than two decades. It has been shown that specific vacuolar sorting signals, in either N-terminal or C-terminal propeptides of plant vacuolar proteins, are crucial for proper recognition and transport of those proteins to target destination (Dice J F. Trends Biochem Sci, 1990, 15:305-309; Chrispeels M J. Annu Rev Plant Physiol Plant Mol Biol, 1991, 42: 21-53; Chrispeels M J, Raikhel N V. Cell, 1992, 68: 613-616; Nakamura K and Matsuoka K. Plant Physiol., 1993, 101: 1-5).

By way of example, a precursor for sporamin A, the storage protein of the tuberous roots of sweet potato deposited in the vacuole, is synthesized on membrane-bound polysomes and has an extra peptide of 37 amino acids at the N-terminus of the mature form, which can be divided into an N-terminal putative signal peptide sequence (residues −37 to −17) and a segment enriched with charged amino acids (residues −16 to −1) (Hattori, T., et al. Plant Mol. Biol., 1985, 5, 313-320). The propeptide of a precursor to sporamin, a storage protein of sweet potato, is required for targeting of sporamin to the vacuole in transformed tobacco cells (Matsuoka K, Nakamura K., Proc Natl Acad Sci USA. 1991, 188: 834-838). In an embodiment, a sporamin A sequence is used in a composition emcompassed herein. In another embodiment, a sporamin B sequence is used in a composition encompassed herein. In an embodiment, two or more sporamin sequences are used in a composition, wherein the composition comprises at least two sporamin A sequences, at least two sporamin B sequences, or at least one sporamin A and one sporamin B sequence. In an embodiment, a sequence comprising at least a portion of sporamin A and/or at least a portion of sporamin B is used in a composition encompassed herein.

By way of another example, a fusion gene consisting of an inducible GAL 10 promoter and sporamin cDNA was introduced into *Saccharomyces cerevisiae* resulting in successful delivery of a sweet potato storage protein sporamin, to the vacuole in yeast cells (Matsuoka K, Nakamura K. Plant Cell Physiology, 1992, 33, 4: 453-462.). It has also been demonstrated that specific accumulation of sporamine from barley in transgenic tobacco cell vacuoles was facilitated by recognition of specialized amino-terminal propeptides (Schroeder M., Borkhsenious N., Matsuoka K, Nakamura K., and Raikhel N. Plant Physiology, 1993, 101: 451-458).

In an embodiment, a vacuolar targeting sequence comprises a C-terminal propeptide of barley lectin. A C-terminal propeptide of barley lectin (Bednarek, S. Y., et al., Plant Cell, 1990, 2: 1145-1155) was demonstrated to cause secretion of the mutated proteins in transgenic tobacco, demonstrating that the propeptides of these storage proteins carry sequences necessary for vacuolar targeting. In an embodiment, a vacuolar targeting sequence comprises a C-terminal extension of tobacco chitinase A. A short C-terminal extension of tobacco chitinase A has been shown to function as a vacuolar targeting signal. It is necessary for the correct vacuolar targeting of chitinase A and sufficient to target an unrelated, normally secreted chitinase of class III to the vacuole. (J-M Neuhaus, et al., Proc. Natl. Acad. Sci. USA, 1991, 88:10362-10366). In an embodiment, a vacuolar targeting sequence comprises an N-terminal vacuolar targeting sequence derived from a potato proteinase inhibitor. Targeting of a vacuole was achieved by use of N-terminal vacuolar targeting sequences derived from potato proteinase inhibitors, which are known to target constitutively to vacuoles in potato tubers and, under wound-induction, in tomato leaves (C Murray, et al., Transgenic Research, 2002, 11, 2: 199-214).

In an embodiment of the present disclosure, a gene expression cassette is provided which enhances content of biofuel synthesis precursors in plant biomass, as compared to unmodified plants, wherein the gene expression cassette comprises at least one vacuole-targeting sequence. In another embodiment, a gene expression cassette comprises at least one gene that enhances content of oil biofuel precursors in plant biomass, as compared to unmodified plants, wherein the gene that enhances content of oil biofuel precursors in plant biomass further comprises at least one vacuole-targeting sequence. In an embodiment, a gene comprising the nucleic acid sequence encoding at least one vacuolar targeting sequence is expressed to produce a protein comprising an amino acid vacuolar targeting sequence. In an embodiment, the vacuole-targeting sequence comprises a protein that is transported to and accumulates within a vacuole in the cell in which it is expressed. In an embodiment, the vacuole-targeting sequence comprises a protein that is transported to and accumulates within a vacuole in a cell other than the cell in which the protein is expressed.

In an embodiment, a vacuolar targeting sequence comprises the sequence set forth from nucleotide 80 to nucleotide 125 of the sequence set forth in FIG. 1A. In an embodiment, a vacuolar targeting sequence comprises a derivative of the sequence set forth from nucleotide 80 to nucleotide 125 of the sequence set forth in FIG. 1A. In an embodiment, a vacuolar targeting sequence comprises at least a portion of the sequence set forth from nucleotide 80 to nucleotide 125 of the sequence set forth in FIG. 1A.

Following Agrobacterium-mediated transformation, the resulting tobacco plants can be tested for the presence of introduced genes by PCR, and grown in the greenhouse for further analysis with respect to quantity and quality of lipid and sugar accumulated in their biomass. Lipid-enhanced plants can be characterized for the number and size of oil bodies by a simple microscopic test using lipid-specific dye Sudan IV. The precise quantitative lipid estimations and fatty acid composition analysis can be performed by gas chromatography mass spectrometry (GC-MS). The total sugar content in sugar-enhanced plants can be evaluated by refractometer, and the isomaltulose can be measured by liquid chromatography. Following the preliminary selection for the highest lipid and sugar content, the best lines can be self-pollinated for genetic stabilization of the new trait. The seeds of the resulting F1 generation plants can be used for selection of high-performing homogeneous lines, which can be further used in cross-pollinations to generate tobacco feedstock that combine high-lipid and high-sugar traits. Following the detailed metabolite analysis in the generated plants, the juice of the best high-sugar, high-oil lines can be fermented to evaluate ethanol yield.

In an embodiment, a method is provided for increasing energy density of plant biomass that can be used for production of renewable fuel, such as biodiesel oil and/or ethanol. The disclosure encompassed herein can provide that in transgenic plants, with enhanced oil biosynthesis precursor content in its biomass, such as simultaneously enhanced sugar and oil (e.g., triacylglycerides), this increases the pool of metabolites for ethanol fermentation and/or increases oil accumulation, leading to an increase in energy density. The disclosure encompassed herein provides transgenic plants whose sucrose is converted into isomaltulose as a result of the expression of technologically introduced SI DNA sequences. In this way, among other possibilities, expression of SI DNA sequences leads to increased energy density.

In an embodiment, the present disclosure relies on using plants with enhanced biofuel synthesis precursor content, such as simultaneously enhanced sugar and oil (e.g., triacylglycerides) in its biomass, that increase pool of metabolites for both ethanol fermentation and increasing oil accumulation. The enhanced biofuel synthesis precursor plants can be naturally selected varieties or genetically engineered for higher enhanced biofuel synthesis precursor accumulation. Particularly, genetic engineering for enhanced sugar accumulation can be achieved, but is not limited to, by overexpressing a bacterial enzyme SI, or amylase. In an embodiment, genetic engineering for enhanced sugar accumulation can be achieved, by overexpressing a bacterial enzyme SI comprising a vacuolar-targeting sequence, which directs the expressed enzyme to one or more vacuoles in the cell. In an embodiment, a cell comprises a central vacuole, and the expressed enzyme comprising a vacuolar-targeting sequence is directed to the central vacuole. In an embodiment, a cell comprises at least two vacuoles, one of which is optionally a central vacuole, and the expressed enzyme comprising a vacuolar-targeting sequence is directed to the central vacuole. In an embodiment, a cell comprises at least two vacuoles, one of which is optionally a central vacuole, and the expressed enzyme comprising a vacuolar-targeting sequence is directed to at least two of the vacuoles. In an embodiment, a cell comprises at least two vacuoles, one of which is optionally a central vacuole, and the expressed enzyme comprising a vacuolar-targeting sequence is directed to each of the vacuoles.

In an embodiment, the enhanced sugar may be used as precursors for the fatty acids synthesis, which is the basic component of vegetable oil. Oils extracted from the plants of the disclosure encompassed herein may be used for industrial purposes such as heating, producing bio-fuels such as biodiesel fuel, or lubricating applications. As used herein, the term "biofuel synthesis precursor" refers to, for example, sugar.

In one aspect, the present disclosure relates to a genetically modified plant having an increased amount of biofuel synthesis precursors as compared to its non-genetically modified counterpart, and wherein the genetically modified plant is genetically modified to stimulate increased biofuel synthesis precursors accumulation in green plant tissues as compared to its non-genetically modified counterpart. This genetically modified plant preferably has increased expression of a first gene, which increases, for example, sugar production in the plant, such as, but not limited to, a bacterial gene encoding SI, the sequence as set forth in FIG. 1, a non-bacterial gene encoding SI, a gene encoding amylase, and a gene which suppresses starch synthesis.

In an embodiment, the genetically modified plant preferably has increased expression of a first gene, which increases, for example, sugar production in the plant, such as, but not limited to, a bacterial gene encoding SI, the sequence as set forth in FIG. 1, a non-bacterial gene encoding SI, a gene encoding amylase, and a gene which suppresses starch synthesis, further wherein the gene comprises a vacuolar-targeting sequence. In an embodiment, SI localized in the vacuole can act on sucrose to produce isomaltulose. In an embodiment, vacuolar-targeted SI produces isomaltulose in the vacuole.

In the art, it has been demonstrated that higher plants do not readily import or catabolize extracellular isomaltulose (Wu L, Birch R. Plant Physiology, 2011, 157, 4: 2094-2101), indicating little to no permeability of plant cell wall and membranes toward isomaltulose. It has also been shown that, in transgenic tobacco, isomaltulose does not penetrate the vacuole, although it was found in high concentrations in other cellular and subcellular compartments (Bornke F, Hajrezaei M, Heineke D, Melzer M, Herbers K, Sonnewald U. Planta, 2002, 214, 3: 356-364.). Additionally, it was found that isomaltulose, a foreign to plant cells substance, is not recognized by sucrose transporters despite really minor structural differences between the two (Srivastava A, Ganesan S, Ismail I, Ayre B. Plant Physiology, 2008, 148: 200-211.).

In one embodiment, a first gene is operably linked to a first promoter which regulates expression of the gene, such as a promoter selected from the group consisting of a constitutive promoter, developmentally regulated promoter, tissue-specific promoter or an inducible promoter. This genetically modified plant may also include a second gene, which encodes, for example, a transcription factor which regulates seed development of the genetically modified plant. The second gene may be, for example, a gene encoding a polypeptide wherein the polypeptide is an enzyme involved in lipid metabolism, in particular, enzymes involved in increased oil accumulation (Beisson et al., Plant Physiol., 132(2), 681-697 (2003); Thelen and Ohlrogge, Metabolic Engineering, 4, 12-21 (2002); Baud et al, Plant J., 33(1), 75-86 (2003); Vigeolas et al., Plant Biotechnol. J., 5(3), 431-41 (2007)). In preferred embodiments, the enzyme is selected from the group consisting of a hydrolase and an acyl transferase and wherein the gene is operably linked to a promoter. In another embodiment, the polypeptide is an esterase, a thioesterase, lauryl-acyl carrier protein thioesterase, acyl CoA:diacylglycerol acyltransferase or Sn-2 acyltransferase. Preferably, a diacylglycerol acyltransferase of plant, yeast or animal origin is used. The second gene may be operably linked to a second promoter, preferably an inducible promoter.

In another embodiment, a second gene may encode an esterase, a thioesterase, lauryl-acyl carrier protein thioesterase, acyl CoA:diacylglycerol acyltransferase or Sn-2 acyltransferase. Preferably, a diacylglycerol acyltransferase of plant, yeast or animal origin is used.

In one embodiment, the genetically modified plant has been modified to increase the content of biofuel synthesis precursors in plant biomass, as compared to unmodified plants.

In one embodiment, the genetically modified plant has increased expression of a gene encoding a polypeptide wherein the polypeptide is an enzyme involved in sugar metabolism, e.g. SI. Proteins with SI activity catalyze the isomerization of the disaccharide sucrose to other disaccharides. In this case, the α1-β2-glycosidic bond between the two monosaccharide units of sucrose, namely the glycosidic bond between glucose and fructose, is converted into another glycosidic bond between two monosaccharide units. Especially, SIs, also known as sucrose mutases, catalyze the rearrangement into an α1-α6 bond and/or an α1-α1 bond. The disaccharide isomaltulose is formed as a result of isomerization to an α1-α6 bond, whereas the disaccharide trehalulose is formed during the rearrangement to an α1-α1 bond. In an embodiment, a gene encoding a SI is a bacterial gene. In an embodiment, a gene encoding a SI is a non-bacterial gene. In an embodiment, a gene encoding a SI is a synthetic gene. In an embodiment, a gene encoding a SI comprises the nucleic acid sequence set forth in FIG. 1. In an embodiment, a gene encoding a SI is the nucleic acid sequence set forth in FIG. 1.

Examples of organisms whose cells contain nucleic acid sequences coding for a protein having SI activity especially include micro-organisms of the genus *Protaminobacter, Erwinia, Serratia, Leuconostoc, Pseudomonas, Agrobacterium, Klebsiella* and *Enterobacter*. Here particular mention may be made of the following examples of such micro-organisms: *Protaminobacter rubrum* (CBS 547, 77), *Erwinia rhapontici* (NCPPB 1578), *Serratia plymuthica* (ATCC 15928), *Serratia marcescens* (NCIB 8285), *Leuconostoc mesenteroides* NRRL B-521f (ATCC 10830a), *Pseudomonas mesoacidophila* MX-45 (FERM 11808 or FERM BP 3619), *Agrobacterium radiobacter* MX-232 (FERM 12397 or FERM BP 3620), *Klebsiella* subspecies and *Enterobacter* species.

In one embodiment, the genetically modified plant has increased expression of a gene encoding a polypeptide wherein the polypeptide is an enzyme involved in sugar metabolism, e.g. amylase. Amylase is an enzyme that catalyzes the hydrolysis of starches into sugars. Amylases hydrolyze internal α-1,4-glucosidic linkages in starch, largely at random, to produce smaller molecular weight maltodextrins. As used herein, the term "amylase" encompasses enzymes (e.g., E.C. class 3.2.1.1) having α-amylase activity, for example, α-amylases capable of hydrolyzing internal α-1,4-glucan links in polysaccharides, including amylase enzymes capable of hydrolyzing starch to sugars at alkaline pHs or at acidic pHs. These enzymes have also been described as those effecting the exohydrolysis or endohydrolysis of 1,4-α-D-glucosidic linkages in polysaccharides containing 1,4-α-linked D-glucose units. Another term used to describe these enzymes is "glycogenase."

The α-amylase enzymes useful herein are characterized and classified according to the number and/or type of hydrolysis products resulting from liquefaction of starch-containing plant material in the presence of the α-amylase enzyme.

Suitable classes of α-amylase enzymes include, for example, the α-amylases derived from *Bacillus* sp. (e.g., such as *Bacillus licheniformis, Bacillus amyloliquefaciens, Bacillus subtilis,* or *Bacillus stearothermophilus*), or *Aspergillus*.

As used herein, the term "plant" refers to whole plants, plant organs (i.e., leaves, stems, flowers, roots, etc.), seeds and plant cells (including tissue culture cells), and progeny of same. The class of plants that can be used in the method of the disclosure encompassed herein is generally as broad as the class of higher plants amenable to transformation techniques, including both monocotyledonous and dicotyledonous plants, as well as certain lower plants such as algae. Suitable plants include plants of a variety of ploidy levels, including polyploid, diploid and haploid. The term "transgenic plant" refers to a plant modified to express one or more genes. Although a variety of plants may be used in the disclosure encompassed herein, the genetically modified plants of the present disclosure are preferably selected from the group of tobacco, maize, pea, canola, Indian mustard, millet, sunflower, hemp, switchgrass, duckweed, sugarcane, *sorghum*, and sugar beet. Preferably the plant encompassed herein is selected from tobacco, hemp, switchgrass and duckweed because they are not food-generating crops for humans and because they can be grown on agriculturally marginal land.

The term "green biomass" means those parts of plants involved in photosynthesis (e.g., and stems and leaves of higher plants and aquatic plants such as algae).

The term "genetically modified" refers to plants in which a gene has been added or modified so as to provide the desired characteristics above. As used herein, the term "gene" refers to an element or combination of elements that are capable of being expressed in a cell, either alone or in combination with other elements. In general, a gene comprises (from the 5' to the 3' end): (1) a promoter region, which includes a 5' non-translated leader sequence capable of functioning in plant cells; (2) a structural gene or polynucleotide sequence, which codes for the desired protein; and (3) a 3' non-translated region, which typically causes the termination of transcription and the polyadenylation of the 3' region of the RNA sequence. Each of these elements is operably linked by sequential attachment to the adjacent element. In an embodiment, a gene comprising the above elements is inserted by standard recombinant DNA methods into a plant expression vector. In another embodiment, a gene comprising the above elements is inserted into a transformation vector.

As used herein, "polypeptide" is used interchangeably with protein, peptide and peptide fragments. "Polypeptides" include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. The polypeptides include natural peptides, recombinant peptides, synthetic peptides, or a combination thereof.

As used herein "promoter" refers to a region of a DNA sequence active in the initiation and regulation of the expression of a structural gene. This sequence of DNA, usually upstream to the coding sequence of a structural gene, controls the expression of the coding region by providing the recognition for RNA polymerase and/or other elements required for transcription to start at the correct site.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope encompassed herein are alterations of a wild type or synthetic gene, including but not limited to deletion, insertion, substitution of one or more nucleotides, or fusion to other polynucleotide sequences, provided that such changes in the primary sequence of the gene do not substantially alter the expressed polypeptide's activity.

As disclosed herein, "substantially homologous sequences" include those sequences which have at least about 50%, homology, preferably at least about 60%, more preferably at least about 70% homology, even more preferably at least about 80% homology, and most preferably at least about 95% or more homology to the polynucleotides encompassed herein.

In one aspect, the disclosure encompassed herein relates to a genetically modified plant having enhanced content of biofuel synthesis precursors as compared to its non-genetically modified counterpart, and wherein the genetically modified plant is genetically modified to stimulate increased biofuel precursor and/or biofuel accumulation in green plant tissues as compared to its non-genetically modified counterpart. This genetically modified plant preferably has increased expression of a first gene, which increases for example, sugar production in the plant, such as by expression of a polypeptide selected from the group consisting of a bacterial SI, the sequence as set forth in FIG. 1, a non-bacterial SI, a gene encoding amylase, and a polypeptide which suppresses starch synthesis. In an embodiment, the genetically modified plant preferably has increased expression of a first gene, which increases, for example, sugar production in the plant, such as by expression of a polypeptide selected from the group consisting of, for example a gene encoding SI, and/or the sequence as set forth in FIG. 1, further wherein the gene encodes a polypeptide comprising a vacuolar-targeting sequence. This first gene is operably linked to a first promoter which regulates expression of the gene, such as a promoter selected from the group consisting of a constitutive promoter, developmentally regulated promoter, tissue-specific promoter or an inducible promoter.

In an embodiment, the genetically modified plant has increased expression of a gene encoding a transcription factor which regulates seed development in the plant. These transcription factors may be involved in a variety of activities in the plant. In particular, such transcription factors may be necessary to turn on the embryogenesis program which leads to seed development and maturation. Preferably, the transcription factor is operably linked to an inducible promoter. In another embodiment, the transcription factor is LEC2 (Lotan T, Ohto M, Yee K M, West M A, Lo R, Kwong R W, Yamagishi K, Fischer R L, Goldberg R B, Harada J J. *Arabidopsis* LEAFY COTYLEDON1 is sufficient to induce embryo development in vegetative cells. Cell. 1998 93(7): 1195-205) or LEC1, FUS3 or WR1.

A genetically modified plant as encompassed herein may also include at least a second gene. The second gene may be selected from the group consisting of, for example, a hydrolase and an acyl transferase, and wherein the gene is operably linked to a promoter. In another embodiment, the polypeptide is an esterase, a thioesterase, lauryl-acyl carrier protein thioesterase, acyl CoA:diacylglycerol acyltransferase or Sn-2 acyltransferase. Preferably, a diacylglycerol acyltransferase of plant, yeast or animal origin is used. The second gene may be operably linked to a second promoter, preferably an inducible promoter. The second gene may be operably linked to at least a second promoter, preferably an inducible promoter.

The first and second genes can be introduced in any order into the plant. For example, the first gene can be introduced into plant cells followed by selection of cells expressing high levels of the first gene. Optionally, these plant cells can be used to regenerate the plant at this stage. These plant cells can then be transformed with the second gene, followed by selection of cells expressing high levels of the second gene. Such a strategy can also be employed transforming the second first, and the first gene last. In embodiments encompassing genes encoding polypeptides comprising one or more vacuole-targeting sequences, the vacuole targeting sequence is preferably fused to the N-terminal portion of the protein of interest. However, it will be understood to the skilled artisan, in view of the disclosure set forth herein, that one or more vacuole-targeting sequences can be fused to the protein of interest in various locations, including, but not limited to, the C-terminus of the protein, as well as inserted into a non-terminal portion of the protein. The skilled artisan will understand how to evaluate the resultant fusion protein and determine the integrity, activity, and usefulness of any such fusion protein. Such fusion proteins may be used as-is, or further processing may be used to remove a portion or all of the vacuolar-targeting sequence from the protein. The removal of such sequences may be intentionally conducted, may occur naturally in the cell, or may occur by a combination of the two methods. The skilled artisan will understand how to remove such sequences from any fusion protein made according to the present disclosure.

Another strategy employs a single transformation (or introduction) of both the first and second genes into the plant. The first and second genes can be transduced in a single vector or in two separate vectors.

Cells are then selected that express both genes at high levels, followed by regeneration of the plant cells into plants.

Another strategy employs separate transformation (introduction) of the two genes into two different sets of plant cells, followed by regeneration of both sets of plant cells into plants. These transgenic plants are then cross-pollinated with each other in order to generate a transgenic plant comprising both genes.

According to another aspect, encompassed herein are plant expression vectors carrying the gene constructs encompassed herein. The gene constructs encompassed herein comprise polynucleotides which enhance content of biofuel synthesis precursors. The gene constructs encompassed herein may further comprise polynucleotides encoding hydrolase enzymes, acyl transferase enzymes, and transcription factors, for example lauryl-acyl carrier protein thioesterase, acyl CoA:diacylglycerol acyltransferase, Sn-2 acyltransferase, and LEC2. The regulatory control elements are operably linked to polynucleotides encoding hydrolase enzymes, acyl transferase enzymes, and transcription factors genes. The function of the regulatory control elements, by way of example and not limitation, includes avoiding homology-based gene silencing, increasing hydrolase enzymes, acyl transferase enzymes, and transcription factors gene expression levels, and inducing compartment-specific accumulation, among others.

In one embodiment, the regulatory control elements are operably linked to polynucleotides encoding a bacterial SI, a bacterial pal, a bacterial pal I, the sequence as set forth in FIG. 1, amylase, or a polypeptide which suppresses starch synthesis. In another embodiment, regulatory control elements are operably linked to polynucleotides encoding polynucleotides encoding hydrolase enzymes, acyl transferase enzymes, and transcription factors, for example lauryl-acyl carrier protein thioesterase, acyl CoA:diacylglycerol acyltransferase, Sn-2 acyltransferase, and LEC2. In one embodiment, the regulatory control elements comprise a translation alfalfa mosaic virus untranslated leader sequence AMV activator, an ER retention signal KDEL, or both.

Expression vectors are defined herein as DNA sequences that are required for the transcription of cloned copies of genes and the translation of their mRNAs in an appropriate host. Such expression vectors are used to express eukaryotic and prokaryotic genes in plants. Expression vectors include, but are not limited to, cloning vectors, modified cloning vectors, specifically, designed plasmids or viruses.

According to one embodiment, there are provided plant expression vectors containing one or more gene constructs encompassed herein. The plant expression vectors encompassed herein contain the necessary elements to accomplish genetic transformation of plants so that the gene constructs are introduced into the plant's genetic material in a stable manner, i.e., a manner that will allow the genes to be passed on to the plant's progeny. The design and construction of the expression vector influence the integration of the gene constructs into the plant genome and the ability of the genes to be expressed by plant cells.

Also encompassed herein is a method of making biofuels from plants transformed according to the teachings encompassed herein. To make biofuels, oils may be extracted from such plants and may be converted to biofuels. Independent of the type of plant, there are several methods for extracting oils from green biomass. One way is physical extraction, which often does not use solvent extraction. It is a "traditional" way using several different types of mechanical extraction. Expeller pressed extraction is a common type, as are the screw press and ram press extraction methods. The amount of oil extracted using these methods varies widely, depending upon the plant material and the mechanical process employed. Mechanical extraction is typically less efficient than solvent extraction described below.

In solvent extraction, an organic solvent (e.g., hexane) is mixed with at least the genetically modified plant green biomass, preferably after the green biomass is dried and ground. Of course, other parts of the plant besides the green biomass (e.g., oil-containing seeds) can be ground and mixed in as well. The solvent dissolves the oil in the biomass and the like, which solution is then separated from the biomass by mechanical action (e.g., with the pressing processes above). This separation step can also be performed by filtration (e.g., with a filter press or similar device) or centrifugation etc. The organic solvent can then be separated from the oil (e.g., by distillation). This second separation step yields oil from the plant and can yield a re-usable solvent if one employs conventional vapor recovery.

In some embodiments, biodiesel oil can be made from oils extracted from plants transformed according to the disclosure encompassed herein. Biodiesel oil is currently produced from soybean seeds following strict federal specifications (ASTM D6751). Conventionally, biodiesel is made through transesterification process whereby vegetable oil is reacted with methanol in the presence of sodium hydroxide. The process results in producing two products—methyl esters (the chemical name for biodiesel) and glycerin (a valuable byproduct usually sold to be used in soaps and other products). This conventional process can be adapted to the production of biofuel oil from tobacco green biomass (or other green biomass from other plants transformed in accordance with the present disclosure). Caustic compounds and water are added to the oil before carrying out the transesterification step in a well-established industry process known as "alkali refining" (Ericson, 1995).

As to plants transformed according to the disclosure encompassed herein, specifically designed expression vectors can allow the shuttling of DNA between hosts, such as between bacteria and plant cells. According to one embodiment, the expression vector contains an origin of replication for autonomous replication in host cells, selectable markers, a limited number of useful restriction enzyme sites, active promoter(s), and additional regulatory control sequences.

Preferred among expression vectors, in certain embodiments, are those expression vectors that contain cis-acting control regions effective for expression in a host operatively linked to the polynucleotide encompassed herein to be expressed. Appropriate trans-acting factors are supplied by the host, supplied by a complementing vector or supplied by the vector itself upon introduction into the host.

In certain preferred embodiments in this regard, the expression vectors provide for specific expression. Such specific expression is an inducible expression, cell or organ specific expression, host-specific expression, or a combination thereof.

In one embodiment, the plant expression vector is an Agrobacterium-based expression vector. Various methods are known in the art to accomplish the genetic transformation of plants and plant tissues by the use of Agrobacterium-mediated transformation systems, i.e., *A. tumefaciens* and *A. rhizogenesis*. *Agrobacterium* is the etiologic agent of crown gall, a disease of a wide range of dicotyledons and gymnosperms that results in the formation of tumors or galls in plant tissue at the site of infection. *Agrobacterium*, which normally infects the plant at wound sites, carries a large extrachromosomal element called Ti (tumor-inducing) plasmid.

Ti plasmids contain two regions required for tumor induction. One region is the T-DNA (transferred-DNA) which is the DNA sequence that is ultimately found stably transferred to plant genomic DNA. The other region is the vir (virulence) region which has been implicated in the transfer mechanism. Although the vir region is absolutely required for stable transformation, the vir DNA is not actually transferred to the infected plant. Transformation of plant cells mediated by infection with *A. tumefaciens* and subsequent transfer of the T-DNA alone have been well documented. See, i.e., Bevan et al. (1982) Int. Rev. Genet. 16:357, incorporated herein by reference in its entirety.

*A. rhizogenes* has also been used as a vector for plant transformation. This bacterium, which incites root hair formation in many dicotyledonous plant species, carries a large extrachromosomal element called a Ri (root-inducing) plasmid which functions in a manner analogous to the Ti plasmid of *A. tumefaciens*. Transformation using *A. rhizogenes* has developed analogously to that of *A. tumefaciens* and has been successfully utilized to transform the plant encompassed herein.

*Agrobacterium* systems have been developed to permit routine transformation of a variety of plant tissues. Representative tissues transformed by this technique include, but are not limited to, tobacco, tomato, sunflower, cotton, rapeseed, potato, poplar, and soybean, among others. This technique can be used to modify the other plants listed earlier in this specification having green biomass.

Promoters are responsible for the regulation of the transcription of DNA into mRNA. A number of promoters which function in plant cells are known in the art, and may be employed in the practice of the present disclosure as described above. These promoters are obtained from a variety of sources such as, for example, plants or plant viruses, bacteria, among others.

Encompassed herein is the use of constitutive promoters, inducible promoters, or both. In general, an "inducible promoter" is a promoter that is capable of directly or indirectly activating transcription of one or more DNA sequences or genes in response to an inducer such as a chemical (e.g. tetracycline, ethanol or a plant hormone). In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducible promoter can be selected from a chemically-inducible promoter such as a tetracycline-inducible promoter, an ethanol-inducible promoter, and a hormone-inducible promoter.

The inducible promoter can also be selected from a physiologically-inducible promoter such as a heat-inducible promoter, a wound-inducible promoter, a senescence-inducing promoter, and a maturation-inducing promoter.

Inducible promoters are determined using any methods known in the art. For example, the promoter may be operably associated with an assayable marker gene such as GUS (glucouronidase), the host plant can be engineered with the construct; and the ability and activity of the promoter to drive the expression of the marker gene in the harvested tissue under various conditions assayed.

A plant cell containing an inducible promoter is exposed to an inducer by externally applying the inducer to the cell or plant such as by spraying, harvesting, watering, heating or similar methods. In addition, inducible promoters include tissue specific promoters that function in a tissue specific manner to regulate the gene of interest within selected tissues of the plant Examples of such tissue specific promoters include seed, flower or root specific promoters as are well known in the field.

A "constitutive promoter" is a promoter that directs the expression of a gene throughout the various parts of a plant and continuously throughout plant development.

In one embodiment, promoters are tissue-specific. Non-tissue-specific promoters (i.e., those that express in all tissues after induction), however, are preferred. More preferred are promoters that additionally have no or very low activity in the uninduced state. Most preferred are promoters that additionally have very high activity after induction. Particularly preferred among inducible promoters are those that can be induced to express a protein by environmental factors that are easy to manipulate.

In one embodiment, one or more constitutive promoters are used to regulate expression of the genes in a plant.

Examples of an inducible and/or constitutive promoters include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), the promoter isolated from the chlorophyll a/b binding protein, proteinase inhibitors (PI-I, PI-II), defense response genes, phytoalexin biosynthesis, phenylpropanoid phytoalexin, phenylalanine ammonia lyase (PAL), 4-coumarate CoA ligase (4CL), chalcone synthase (CHS), chalcone isomerase (CHI), resveratrol (stilbene) synthase, isoflavone reductase (IFR), terpenoid phytoalexins, HMG-CoA reductase (HMG), casbene synthetase, cell wall components, lignin, phenylalanine ammonia lyase, cinnamyl alcohol dehydrogenase (CAD), caffeic acid o-methyltransferase, lignin-forming peroxidase, hydroxyproline-rich glycoproteins (HRGP), glycine-rich proteins (GRP), thionins, hydrolases, lytic enzymes, chitinases (PR-P, PR-Q), class I chitinase, basic, Class I and II chitinase, acidic, class II chitinase, bifunctional lysozyme, .beta.-1,3-Glucanase, *arabidopsis*, .beta.-fructosidase, superoxide dismutase (SOD), lipoxygenase, prot., PR1 family, PR2, PR3, osmotin, PRS, ubiquitin, wound-inducible genes, win 1, win2 (hevein-like), wun1, wun2, nos, nopaline synthase, ACC synthase, HMG-CoA reductase hmg1, 3-deoxy-D-arabino-heptulosonate-7-phosphate synthase, HSP7033, Salicylic acid inducible acid peroxidase, PR-proteins, glycine-rich protein, methyl jasmonate inducible, vspB.sup.42, heat-shock genes, HSP70, cold-stress inducible, drought, salt stress, hormone inducible, gibberellin, α-amylase, abscisic acid, EM-1, RAB, LEA genes, ethylene, phytoalexin biosyn genes, or a combination thereof.

The above-noted promoters are listed solely by way of illustration of the many commercially available and well known plant promoters that are available to those of skill in the art for use in accordance with this aspect of the present disclosure. It will be appreciated that any other plant promoter suitable for, for example, introduction, maintenance, propagation or expression of a polynucleotide or polypeptide of the disclosure encompassed herein in plants may be used in this aspect of the disclosure encompassed herein.

In another embodiment, the promoter is selected from the group of promoters that direct constitutive gene expression throughout green plant tissues, particularly leaves and stems. This group is exemplified by the strong promoters of plant virus origin, such as the 35S promoter from cauliflower mosaic virus (CaMV), the cassava vein mosaic virus (CsVMV) promoter, the sugarcane bacilliform badnavirus (ScBV) promoter, or similar plant virus promoters (Samac D A, Tesfaye M, Dornbusch M, Saruul P, Temple S J. Transgenic Res. 2004 August; 13(4):349-61.) In addition such promoter can be a promoter of small subunit of ribulose-1, 5-bisphosphate carboxylase/oxygenase (Rubisco), that drives transgene in a light-responsive and circadian manner (Tung S A, Smeeton R, White C A, Black C R, Taylor I B, Hilton H W, Thompson A J. Plant Cell Environ. 2008 Apr. 23). Such promoter can also be selected from a histone gene promoter, such as H2B promoter (Rasco-Gaunt S, Liu D, Li C P, Doherty A, Hagemann K, Riley A, Thompson T, Brunkan C, Mitchell M, Lowe K, Krebbers E, Lazzeri P, Jayne S, Rice D. Plant Cell Rep. 2003 February; 21(6):569-760; In addition such a promoter can be selected from tobacco eLF4A-10 promoter (Tian L, Wu K, Hannam C, Latoszek-Green M, Sibbald S, Hu M, Brown D C, Mild B. J Plant Physiol. 2005 December; 162(12):1355-66.) or a tobacco cryptic constitutive promoter, tCUP (Foster E, Hattori J, Labbe H, Ouellet T, Fobert P R, James L E, Iyer V N, Mild B L. Plant Mol Biol. 1999 September; 41(1):45-55.). Another such promoter is the ibAGP1 promoter (Kwak M S, Oh M J, Lee S W, Shin J S, Paek K H, Bae J M. A strong constitutive gene expression system derived from ibAGP1 promoter and its transit peptide. Plant Cell Rep. 2007 August; 26(8):1253-62.) or a promoter that controls the expression of VR-ACS1 from mung bean (Cazzonelli C I, McCallum E J, Lee R, Botella J R. Transgenic Res. 2005 December; 14(6):941-67.). Another such promoter is a ubiquitin promoter (Belknap W, Rockhold D, McCue K. Biotechniques. 2008 May; 44(6):753-6.)

Examples of nucleotide sequences that influence the regulation of heterologous genes include enhancers or activating regions, such as those derived from CaMV 35S, opine synthase genes or other plant genes (U.S. Pat. Nos. 5,106,739; 5,322,938; 5,710,267; 5,268,526; 5,290,294). Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., Plant Cell Physiol., 35:773-778 (1994)), the Cab-1 promoter from wheat (Fejes et al., Plant Mol. Biol., 15:921-932 (1990)), the CAB-1 promoter from spinach (Lubberstedt et al., Plant Physiol., 104:997-1006 (1994)), the cab1R promoter from rice (Luan et al., Plant Cell, 4:971-981 (1992)), the pyruvate orthophosphate dikinase (PPDK) promoter from corn (Matsuoka et al., Proc. Natl. Acad. Sci. USA, 90:9586-9596 (1993)), the tobacco Lhcb1*2 promoter (Cerdan et al., Plant Mol. Biol., 33:245-255 (1997)), the *Arabidopsis thaliana* SUC2 sucrose-H+ symporter promoter (Truemit et al., Planta, 196:564-570 (1995)), and thylakoid membrane protein promoters from spinach (psaD, psaF, psaE, PC, FNR, atpC, atpD, cab, rbcS).

Additional examples of nucleotide sequences that influence the regulation of heterologous genes include, for example, WRKY sequences. Two WRKY transcription factor genes have been studied: WRKY53 plays an important role in controlling leaf senescence (Hinderhofer et al., "Identification of a Transcription Factor Specifically Expressed at the Onset of Leaf Senescence," Planta 213: 469-473 (2001); Miao et al., "Targets of the WRKY53 Transcription Factor and Its Role During Leaf Senescence in *Arabidopsis*," Plant Mol Biol 55:853-867 (2004); Robatzek et al., "Targets of AtWRKY6 Regulation During Plant Senescence and Pathogen Defense," Genes Dev 16:1139-1149 (2002)), while suppression of WRKY6 expression has little effect on either the onset or the progression of leaf senescence (Hinderhofer et al., "Identification of a Transcription Factor Specifically Expressed at the Onset of Leaf Senescence," Planta 213:469-473 (2001); Miao et al., "Targets of the WRKY53 Transcription Factor and Its Role During Leaf Senescence in *Arabidopsis*," Plant Mol Biol 55:853-867 (2004); Robatzek et al., "Targets of AtWRKY6 Regulation During Plant Senescence and Pathogen Defense," Genes Dev 16:1139-1149 (2002)).

Gene constructs of the disclosure encompassed herein can also include other optional regulatory elements that regulate, as well as engender, expression. Generally such regulatory control elements operate by controlling transcription. Examples of such regulatory control elements include, for example, enhancers (either translational or transcriptional enhancers as may be required), repressor binding sites, terminators, leader sequences, and the like.

Specific examples of these elements include, but are not limited to, the enhancer region of the 35S regulatory region, as well as other enhancers obtained from other regulatory regions, and/or the ATG initiation codon and adjacent sequences. The initiation codon must be in phase with the reading frame of the coding sequence to ensure translation of the entire sequence. The translation control signals and initiation codons are from a variety of origins, both natural and synthetic. Translational initiation regions are provided from the source of the transcriptional initiation region, or from the structural gene. The sequence is also derived from the promoter selected to express the gene, and can be specifically modified to increase translation of the mRNA.

The nontranslated leader sequence is derived from any suitable source and is specifically modified to increase the translation of the mRNA. In one embodiment, the 5' nontranslated region is obtained from the promoter selected to express the gene, the native leader sequence of the gene, coding region to be expressed, viral RNAs, suitable eukaryotic genes, or a synthetic gene sequence, among others. In another embodiment, gene constructs of the disclosure encompassed herein comprise a 3U untranslated region. A 3U untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3U end of the mRNA precursor.

The termination region or 3' nontranslated region is employed to cause the termination of transcription and the addition of polyadenylated ribonucleotides to the 3' end of the transcribed mRNA sequence. The termination region may be native with the promoter region, native with the structural gene, or may be derived from the expression vector or another source, and would preferably include a terminator and a sequence coding for polyadenylation. Suitable 3' nontranslated regions of the chimeric plant gene include, but are not limited to: (1) the 3' transcribed, nontranslated regions containing the polyadenylation signal of *Agrobacterium* tumor-inducing (Ti) plasmid genes, such as the nopaline synthase (NOS) gene, and (2) plant genes like the soybean 7S storage protein genes and the pea small subunit of the ribulose 1,5-bisphosphate carboxylase-oxygenase, among others.

The addition of appropriate introns and/or modifications of coding sequences for increased translation can also substantially improve foreign gene expression. Appropriate introns include, but are not limited to, the maize hsp70 intron, maize adh 1 intron, and rice actin intron.

In one embodiment, the regulatory control elements of the disclosure encompassed herein include an alfalfa mosaic virus untranslated leader sequence and Lys-Asp-Glu-Leu (KDEL) endoplasmic reticulum retention signal operably attached to the N- and C-terminus of heavy chain, respectively.

It has been shown that the inclusion of KDEL or HDEL amino acid sequences at the carboxy terminus of at least one protein enhanced the recognition for that protein by the plant endoplasmic reticulum retention machinery. See, Munro and Pelham (1987) Cell 48:988-997; Denecke et al. (1991) EMBO-J: 11:2345; Herman et al. (1991) Planta 182:305; and Wandelt et al. (1992) The Plant Journal 2:181, each of which is incorporated herein by reference in its entirety.

To aid in identification of transformed plant cells, the gene constructs of the disclosure encompassed herein may be further manipulated to include selectable marker genes that are functional in bacteria, plants or both. Useful selectable markers include, but are not limited to, enzymes which provide for resistance to an antibiotic such as ampicillin resistance gene ($Amp^r$), tetracycline resistance gene ($Tc^r$), cycloheximide-resistance L41 gene, the gene conferring resistance to antibiotic G418 such as the APT gene derived from a bacterial transposon Tn903, the antibiotic hygromycin B-resistance gene, gentamycin resistance gene, and/or kanamycine resistance gene, among others or herbicides, such as phosphinotricine. Similarly, enzymes providing for production of a compound identifiable by color change such as GUS, or luminescence, such as luciferase, are possible.

A selectable marker gene can be used to select transgenic plant cells of the disclosure encompassed herein, which transgenic cells have integrated therein one or more copies of the gene construct of the present disclosure. The selectable or screenable genes provide another check for the successful culturing of cells carrying the genes of interest. Transformed plant calli may be selected by growing the cells on a medium containing, for example, kanamycin.

Host plants are genetically transformed to incorporate one or more gene constructs of the disclosure encompassed herein. There are numerous factors which influence the success of plant transformation. The design and construction of the expression vector influence the integration of the foreign genes into the genome of the host plant and the ability of the foreign genes to be expressed by plant cells. The type of cell into which the gene construct is introduced must, if whole plants are to be recovered, be of a type which is amenable to regeneration, given an appropriate regeneration protocol.

The integration of the polynucleotides encoding the desired gene into the plant host is achieved through strategies that involve, for example, insertion or replacement methods. These methods involve strategies utilizing, for example, direct terminal repeats, inverted terminal repeats, double expression cassette knock-in, specific gene knock-in, specific gene knock-out, random chemical mutagenesis, random mutagenesis via transposon, and the like. The expression vector is, for example, flanked with homologous sequences of any non-essential plant genes, bacteria genes, transposon sequence, or ribosomal genes. Preferably the flanking sequences are T-DNA terminal repeat sequences. The DNA is then integrated in host by homologous recombination occurred in the flanking sequences using standard techniques.

In one embodiment, *Agrobacterium*-based transformation strategy is employed to introduce the gene constructs into plants. Such transformations preferably use binary *Agrobacterium* T-DNA vectors (Bevan (1984) supra), and the co-cultivation procedure (Horsch et al. (1985) Science 227: 1229-1231, incorporated herein by reference in its entirety). Generally, the *Agrobacterium* transformation system is used to engineer dicotyledonous plants. The *Agrobacterium* transformation system may also be used to transform as well as transfer DNA to monocotyledonous plants and plant cells. See, for example, Hernalsteen et al. (1984) EMBO J. 3:3039-3041; Hooykass-Van Slogteren et al. (1984) Nature 311:763-764; Grimsley et al. (1987) Nature 325:1677-179; Boulton et al. (1989) Plant Mol. Biol. 12:3140; Gould et al. (1991) Plant Physiol. 95:426-434, each of which is incorporated herein by reference in its entirety.

In other embodiments, various alternative methods for introducing recombinant nucleic acid constructs into plants and plant cells are also utilized. These other methods are particularly useful where the target is a monocotyledonous plant or plant cell. Alternative gene transfer and transformation methods include, but are not limited to, protoplast transformation through calcium-polyethylene glycol (PEG)- or electroporation-mediated uptake of naked DNA. See, for example, Paszkowski et al. (1984) EMBO J. 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276, each of which is incorporated herein by reference in its entirety. Electroporation of plant tissues are also disclosed in D'Halluin et al. (1992) Plant Cell 4:1495-1505, incorporated herein by reference in its entirety. Additional methods for plant cell transformation include microinjection, silicon carbide mediated DNA uptake (see, for example, Kaeppler et al. (1990) Plant Cell Reporter 9:415-418), and microprojectile bombardment (see, for example, Klein et al. (1988) Proc. Nat. Acad. Sci. USA 85:4305-4309; Gordon-Kamm et al. (1990) Plant Cell 2:603-618, each of which is incorporated herein by reference in its entirety In the case of direct gene transfer, the gene construct is transformed into plant tissue without the use of the *Agrobacterium* plasmids. Direct transformation involves the uptake of exogenous genetic material into plant cells or protoplasts. Such uptake may be enhanced by use of chemical agents or electric fields. The exogenous material may then be integrated into the nuclear genome.

The early work with direct transfer was conducted in the *Nicotiana tabacum* (tobacco) where it was shown that the foreign DNA was incorporated and transmitted to progeny plants. Several monocot protoplasts have also been transformed by this procedure including maize and rice.

Liposome fusion has also been shown to be a method for transforming plant cells. Protoplasts are brought together with liposomes carrying the desired gene. As membranes merge, the foreign gene is transferred to the protoplasts.

Alternatively, exogenous DNA can be introduced into cells or protoplasts by microinjection. In this technique, a solution of the plasmid DNA or DNA fragment is injected directly into the cell with a finely pulled glass needle.

A more recently developed procedure for direct gene transfer involves bombardment of cells by micro-projectiles carrying DNA. In this procedure, commonly called particle bombardment, tungsten or gold particles coated with the exogenous DNA are accelerated toward the target cells. The particles penetrate the cells carrying with them the coated DNA. Microparticle acceleration has been successfully demonstrated to lead to both transient expression and stable expression in cells suspended in cultures, protoplasts, immature embryos of plants including but not limited to onion, maize, soybean, and tobacco.

In addition to the methods described above, a large number of methods are known in the art for transferring cloned DNA into a wide variety of plant species, including gymnosperms, angiosperms, monocots and dicots. Minor variations make these technologies applicable to a broad range of plant species.

The disclosure encompassed herein further relates to transgenic plants, including whole plants, plant organs (i.e., leaves, stems, flowers, roots, etc.), seeds and plant cells (including tissue culture cells), and progeny of same that are transformed with a gene construct according to the disclosure encompassed herein.

Once plant cells have been transformed, there are a variety of methods for regenerating plants. The particular method of regeneration will depend on the starting plant tissue and the particular plant species to be regenerated. In general, transformed plant cells are cultured in an appropriate medium, which contain selective agents such as, for example, antibiotics, where selectable markers are used to facilitate identification of transformed plant cells. Once callus forms, embryo or shoot formation are encouraged by employing the appropriate plant hormones in accordance with known methods, and the shoots transferred to rooting medium for regeneration of plants. The plants are then used to establish repetitive generations, either from seeds or using vegetative propagation techniques. The presence of a desired gene, or gene product, in the transformed plant may be determined by any suitable method known to those skilled in the art. Included in these methods are southern, northern, and western blot techniques, ELISA, and bioassays.

In recent years, it has become possible to regenerate many species of plants from callus tissue derived from plant explants. The plants which can be regenerated from callus include monocots, such as, but not limited to, corn, rice, barley, wheat, and rye, and dicots, such as, but not limited to, sunflower, soybean, cotton, rapeseed and tobacco.

Sunflower is another plant that can be modified consistent with the teaching of the disclosure encompassed herein Sunflower is one of the staple crops used for production of vegetable seed oil. Unlike other oil producing crops such as soybean and rape-seed, sunflower, due to its big size, can also generate a substantial amount of green biomass. Similar to tobacco, sunflower possesses a potent seed biofuel synthesis pathway that can be modified and relocated to green biomass using the genetic modification techniques of the disclosure encompassed herein using the same kinds of gene modifications. At least two protocols for *Agrobacterium*-mediated transformation of sunflower have been developed that can be also be used to modify sunflower to include the novel genetic modifications consistent with the present disclosure: (1) Weber S, Friedt W, Landes N, Molinier J, Himber C, Rousselin P, Hahne G, Horn R. Improved *Agrobacterium*-mediated transformation of sunflower (*Helianthus annuus* L.): assessment of macerating enzymes and sonication. Plant Cell Rep. 2003 January; 21(5):475-82. 2; and (2) Muller A, Iser M, Hess D., Stable transformation of sunflower (*Helianthus annuus* L.) using a non-meristematic regeneration protocol and green fluorescent protein as a vital marker. Transgenic Res. 2001 October; 10(5):435-44.

Industrial hemp is another plant that can be modified consistent with the teaching of the disclosure encompassed herein. It can be grown in many areas of the world. In Europe and Canada it has traditionally been utilized as energy source plant. For example, *Cannabis sativa*, commonly known as "hemp" is included in a list of potential field crops considered as Candidate Energy Crops in the December 1999 California Energy Commission report "Evaluation Of Biomass-To-Ethanol Fuel Potential In California" pg. iv-3]. Genetic transformation of hemp consistent with the teachings of the present disclosure can be performed via *Agrobacterium* [Feeney M., Punja Z. K. Hemp (*Cannabis sativa* L.). In: Methods Mol Biol 2006; 344:373-82].

Corn is another plant that can be transformed consistent with the teachings of the disclosure encompassed herein. Extracting of oil accumulated in corn green biomass from corn plants modified according to this invention can improve efficiency of oil production. Methods for genetic transformation of corn are well established (Ishida Y, Hiei Y, Komari; Nat Protoc. 2007; 2(7):1614-1621). These same methods can be employed to make the novel genetic modifications of the disclosure encompassed herein.

Switchgrass is another plant that can be modified to incorporate the novel genetic modifications of the disclosure encompassed herein. Unmodified switchgrass is a leading energy plant candidate under consideration by United States Department of Energy. Numerous studies are known to use switchgrass for ethanol production, however both oil end ethanol utilization is possible after improving oil content in switchgrass using the methods of the disclosure encompassed herein. Transformation via *Agrobacterium* is also available [Somleva M. N. Switchgrass (*Panicum virgatum* L.). In: Methods Mol Biol. 2006; 344:65-73].

Duck weed (*Lemna* sp.) Aquatic plant *Lemna* has unique, innate characteristics that provide enormous value for biomass production so that it can be modified to include the novel genetic modifications of the disclosure encompassed herein. The advantages include: versatility, fast and flexible operation, low capital costs for facilities, low operating costs, and environmental safety. As a green plant it has similar pathways of oil production, and its oil content can be improved with the techniques of the disclosure encompassed herein. *Agrobacterium*-mediated transformation of *Lemna* was developed [Yamamoto Y. T. et al. In Vitro Cell Dev. Biol. Plant 2001; 37:349-353].

Sugarcane, *sorghum*, and sugar beet are already used as a source for bioethanol; [Hill. J., et al. Proc. Natl. Acad. Sci. USA, 2006, 103:11206-11210], however genetically modifying these plants to incorporate the novel genetic modifications of the disclosure encompassed herein to increase oil in the green biomass of these plants can increase total energy efficiency. Oil production from sugarcane, *sorghum* and sugar beet could be economically feasible after their genetic modification based on the disclosure encompassed herein. Genetic transformation is described for sugarcane [Shrawat A. K., Lorz H. Plant Biotechnol J. 2006, 4(6): 575-603. Review] and sugar beet [Golovko A. E., Dovzhenko A. A., Gleba Yu. Yu. Tsitol Genet. 2005, 39(3): 30-6. Review.].

Several techniques for genetic transformation of *sorghum* have been established (Casas A M, Kononowicz A K, Zehr U B, Tomes D T, Axtell J D, Butler L G, Bressan R A, Hasegawa P M.; Proc Natl Acad Sci USA. 1993 Dec. 1; 90(23):11212-6. 2: Zhao Z Y, Cai T, Tagliani L, Miller M, Wang N, Pang H, Rudert M, Schroeder S, Hondred D, Seltzer J, Pierce D.; Plant Mol Biol. 2000 December; 44(6):789-98. 3: Gao Z, Xie X, Ling Y, Muthukrishnan S, Liang G H.; Plant Biotechnol J. 2005 November; 3(6):591-9.)

It will be appreciated that polypeptides often contain amino acids other than the 20 amino acids commonly referred to as the "naturally occurring" amino acids, and that many amino acids, including the terminal amino acids, may be modified in a given polypeptide, either by natural processes, such as processing and other post-translational modifications, or by chemical modification techniques.

Modifications can occur anywhere in a polypeptide, including the peptide backbone, the amino acid side chains and the amino or carboxyl termini. Blockage of the amino or carboxyl group in a polypeptide, or both, by a covalent modification, occur in natural or synthetic polypeptides. Such modifications may be present in the polypeptides of the present disclosure, as well. In general, the nature and extent of the modifications are determined by the host cell's post-translational modification capacity and the modification signals present in the polypeptide amino acid sequence. It will be appreciated that the same type of modification may be present in the same or varying degrees at several sites in a polypeptide.

Variations in the structure of the polypeptides may arise naturally as allelic variations, as disclosed above, due to genetic polymorphism, for example, or may be produced by human intervention (i.e., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules.

Substitutions may be designed based on, for example, the model of Dayhoff et al. (1978) Atlas of Protein Sequence and Structure, Natl. Biomed. Res. Found. Washington, D.C. These modifications can result in changes in the amino acid sequence, provide silent mutations, modify a restriction site, or provide other specific mutations.

The present disclosure also encompasses plants comprising polynucleotides that correspond to and code for the genes of the present disclosure. Nucleic acid sequences are either synthesized using automated systems well known in the art, or derived from a gene bank.

It will be appreciated that a great variety of modifications have been made to DNA and RNA that serve many useful purposes known to those of skill in the art. The polynucleotides of the disclosure encompassed herein embrace chemically, enzymatically or metabolically modified forms of polynucleotides.

The polynucleotides encompassed herein encode, for example, the coding sequence for the structural gene, and additional coding or non-coding sequences. Examples of additional coding sequences include, but are not limited to, sequences encoding a secretory sequence, such as a pre-, pro-, or prepro-protein sequences. Examples of additional non-coding sequences include, but are not limited to, introns and non-coding 5' and 3' sequences, such as the transcribed, non-translated sequences that play a role in transcription and mRNA processing, including splicing and polyadenylation signals, for example, for ribosome binding and stability of mRNA.

The polynucleotides encompassed herein also encode a polypeptide which is the mature protein plus additional amino or carboxyl-terminal amino acids, or amino acids interior to the mature polypeptide (when the mature form has more than one polypeptide chain, for instance). Such sequences play a role in, for example, processing of a protein from precursor to a mature form, may facilitating protein trafficking, prolonging or shortening protein half-life or facilitating manipulation of a protein for assay or production, among others. The additional amino acids may be processed away from the mature protein by cellular enzymes.

In sum, the polynucleotides encompassed herein encode, for example, a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

The polynucleotides encompassed herein include "variant(s)" of polynucleotides, or polypeptides as the term is used herein. Variants include polynucleotides that differ in nucleotide sequence from another reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference.

Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence. According to one embodiment of the disclosure encompassed herein, there are no alterations in the amino acid sequence of the polypeptide encoded by the polynucleotides of the disclosure encompassed herein, as compared with the amino acid sequence of the wild type or mammalian derived peptide.

The present disclosure further relates to polynucleotides that hybridize to the herein described sequences. The term "hybridization under stringent conditions" according to the disclosure encompassed herein is used as described by Sambrook et al. (1989) Molecular Cloning, A Laboratory Manual, Cold Spring Harbor Laboratory Press 1.101-1.104. Preferably, a stringent hybridization according to the present disclosure is given when after washing for an hour with 1% SSC and 0.1% SDC at 50.degree. C., preferably at 55° C., more preferably at 62° C., most preferably at 68° C. a positive hybridization signal is still observed. A polynucleotide sequence which hybridizes under such washing conditions with the nucleotide sequence shown in any sequence disclosed herein or with a nucleotide sequence corresponding thereto within the degeneration of the genetic code is a nucleotide sequence according to the disclosure encompassed herein.

The polynucleotides encompassed herein include polynucleotide sequences that have at least about 50%, 65%, 70%, 75%, 80%, 85%, 90%, 95%, 98%, 99% or more nucleotide sequence identity to the polynucleotides or a transcriptionally active fragment thereof. To determine the percent identity of two amino acid sequences or two nucleic acid sequences, the sequences are aligned for optimal comparison purposes (i.e., gaps can be introduced in the sequence of a first amino acid or nucleic acid sequence for optimal alignment with a second nucleic acid sequence). The amino acid residue or nucleotides at corresponding amino acid or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100). In one embodiment, the two sequences are the same length.

The determination of percent identity between two sequences also can be accomplished using a mathematical algorithm. One, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST program of Altschul et al. (1990), J. Mol. Biol. 215:403-410. BLAST nucleotide searches can be performed with the NBLAST program, score=100, wordlength=12 to obtain nucleotide sequences homologous to a nucleic acid molecules of the disclosure encompassed herein. The BLAST protein searches can be performed with the XBLAST program, score=50, wordlength=3 to obtain amino acid sequences homologous to a protein molecule of the disclosure encompassed herein. To obtain gapped alignments for comparison purposes, Gapped BLAST can be utilized as described in Altschul et al. (1997) Nucleic Acids Res. 25:3389-3402.

Alternatively, PSI-Blast can be used to perform an iterated search which detects distant relationships between molecules (Id.). When utilizing BLAST, Gapped BLAST and PSI-Blast programs, the default parameters of the respective programs (i.e., XBLAST and NBLAST program can be used (see WWW<dot>NCBI<dot>NLM<dot>NIH<dot>GOV). Another preferred, non-limiting example of a mathematical algorithm utilized for the comparison of sequences is the algorithm of Myers and Miller (1988) CABIOS 4:11-17. Such an algorithm is incorporated into the ALIGN program (version 2.0) which is part of the GCG sequence alignment software package. When utilizing the ALIGN program for comparing amino acid sequences of a PAM 120 weight residue table, a gap length penalty of 12 and a gap penalty of 4 can be used. In an alternate embodiment, alignments can be obtained using the NA-MULTIPLE-ALIGNMENT 1.0 program, using a GapWeight of 5 and a GapLengthWeight of 1.

The invention will be illustrated in more detail with reference to the following Examples, but it should be understood that the present invention is not deemed to be limited thereto.

EXAMPLES

Example 1. Construction of Plant Transformation Expression Cassette

Expression constructs for SI were made in pUC57. The assembly of the expression vectors is depicted in FIG. 2. The pUC57 vector is known and available from Genscript (GenScript USA Inc. 120 Centennial Ave Piscataway, N.J. Catalog #SD1176-50 ug). In order to avoid high sugar concentration interference with plant development, the expression of the SI enzyme was targeted to vacuole. To achieve a higher level of sugar availability in green biomass a bacterial enzyme, SI, that converts sucrose into its storage isomer isomaltulose, has been expressed in tobacco under two different promoters (CaMV35S and Rubisco (RbcS)).

Example 2. Plant Transformation

Tobacco leaf explants (*Nicotiana tabacum* cv. Wisconsin) are used for *Agrobacterium*-mediated transformation (*A. tumefaciens* EHA105), selection and regeneration on MS-based media (Hiatt et al. (1989) Nature 342:76-78) according to the described protocols (Ko et al. (2000). Tobacco transgenic lines are generated by *Agrobacterium*-mediated plant transformation with a vector carrying, for example, SI. Independent transgenic lines were selected on MS medium containing kanamycin (100 microg/ml). Transgenic tobacco lines were later maintained in soil, and subsequent generations (T1 and T2) were obtained by self-Pollination.

The transgenic plants constitutively expressing, for example, SI may then cross-pollinated with the transgenic plants inducibly expressing, for example, an esterase, a thioesterase, lauryl-acyl carrier protein thioesterase, acyl CoA:diacylglycerol acyltransferase, Sn-2 acyltransferase in order to generate a transgenic plant comprising both genes.

Example 3. Molecular Characterization of Transgenic Plants

Figure 4:
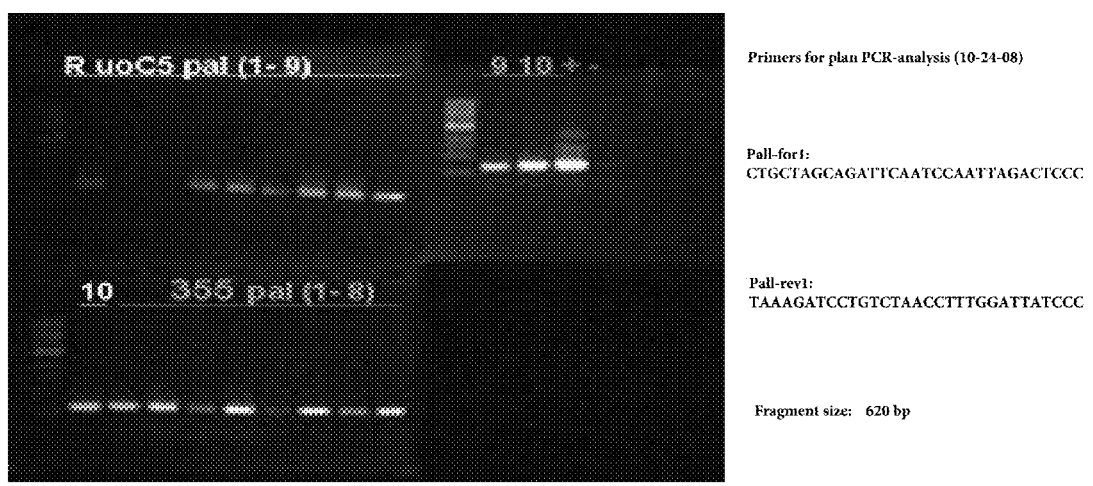
FIG. 4 depicts a PCR analysis of introduced SI gene in transformed tobacco. Fifty eight transgenic tobacco lines have been generated following genetic transformation with a vacuole-targeted SI gene under the control of CaMV 35S (33 lines) and Rubisco (25 lines) promoters. Twenty lines from each transformation (35S-SI and Rubisco-SI) have been confirmed by PCR to contain the SI gene. Primers used for plant PCR analysis include: PalI-for1 (CTGCTAGCAGATTCAATCCAATTAGACTCCC, SEQ ID NO: 4) and PalI-rev1 (TAAAGATCCTGTCTAACCTTTGGATTATCCC, SEQ ID NO: 5). The fragment size was 620 bp.
Figure 5:
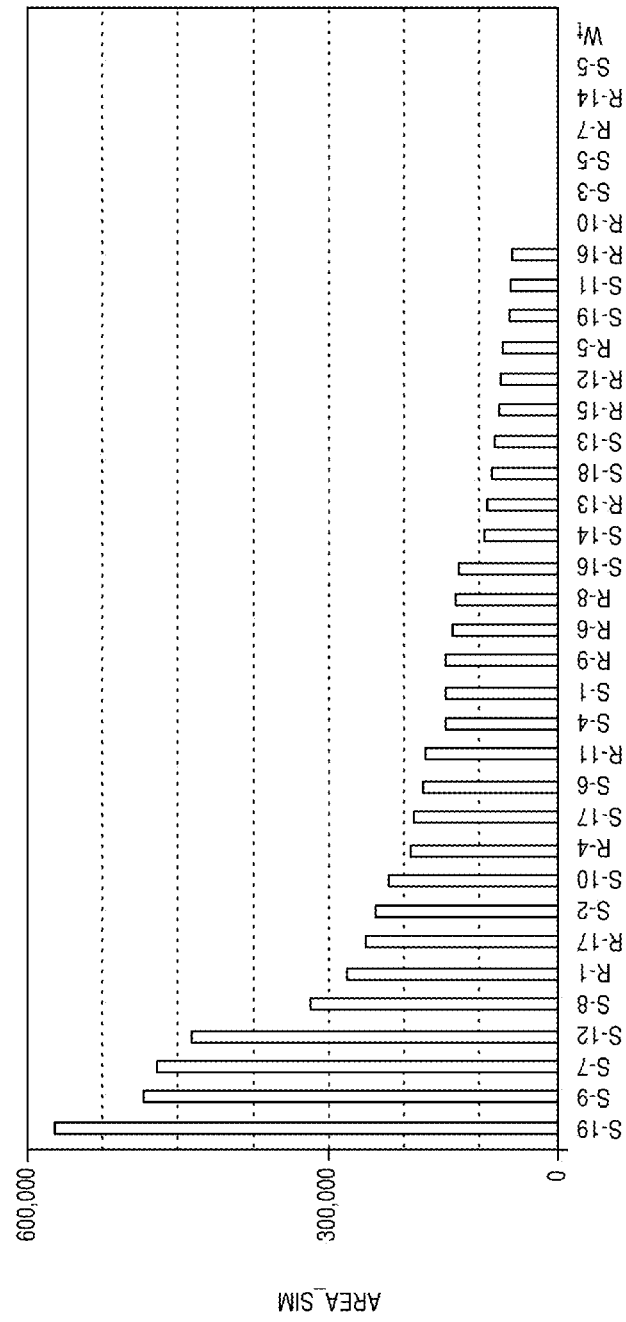
FIG. 5 depicts an analysis of the expression of bacterial SI which leads to accumulation of isomaltulose. Samples from the PCR-positive lines (see FIG. 4) have been collected for sugar analysis, and the results are as shown. Isomaltulose is shown in selected tobacco lines overexpressing PalI gene under the control of 35S promoter (S) and Rubisco promoter (R), as detected by GC-MS. The best expressing lines have been selected for further growth and seed production.

PCR amplification of expressed genes may be performed with genomic DNA of each transgenic line using the same primers as described above. Fifty eight transgenic tobacco lines have been generated following genetic transformation with a vacuole-targeted SI gene under the control of CaMV 35S (33 lines) and Rubisco (25 lines) promoters. Twenty lines from each transformation (CaMV 35S-SI and Rubisco-SI) have been confirmed by PCR to contain the SI gene, examples of the PCR analysis are represented in FIG. 4, which shows PCR analysis of introduced SI gene in transformed tobacco. The best expressing lines have been selected for further growth and seed production.

Example 4. SDS-PAGE and Protein Blot Analysis

One gram of tobacco leaf tissues is ground in liquid nitrogen with 100 microliter of extraction buffer (50 mM Tris, pH 7.5, 250 mM sucrose) containing protease "complete" inhibitor cocktail (Roche, Indianapolis, Ind.). Forty µg of soluble protein (in 10 µl) is resolved by 12% SDS-PAGE and transferred to Immobilon-P Transfer Membrane (Millipore Corp., Bedford, Ma.) using a mini-Protean II™ system (Bio-Rad Labs, Hercules, Calif.) according to the manufacturer's recommendations. The signal is detected using incubation with a HRP-conjugated secondary antibody followed by treatment with "SuperSignal" chemiluminescence substrate (Pierce, Rockford, Ill.).

Example 5. Detection and Measurement of Sugar Production

The amount of sugar in a transgenic plant or plant cell can be determined by known techniques, e.g., by extraction of amino acids and/or sugars followed by gas chromatography-mass spectrometry (GC-MS) or liquid chromatography-mass spectrometry (LC-MS). If desired, the structure of the sugar can be confirmed by GC-MS, LC-MS, nuclear magnetic resonance and/or other known techniques. The total sugar content in sugar-enhanced plants can be evaluated by refractometer, and the isomaltulose will be measured by liquid chromatography.

Example 6. Detection and Measurement of Oil Production

In order to estimate the effect on fatty acid biosynthesis in tobacco, two types of analyses are exemplified. First, the triacylglyceride (TAG) fraction of tobacco biomass may be examined using LC-MS that allows not only quantification of TAG in transgenic lines relative to that in wild-type tobacco, but also determination of the composition of TAG in individual plants. Second, total fatty acid esters, which constitute the biofuel oil used in diesel engines, can be quantified by gas chromatography (GC) following the esterification of extracted fatty acids with acidic methanol (Rogozinski, 1964). For both tests, fatty acids may be isolated from 100 mg of freeze-dried samples collected from 3-month-old plants, using either modified hexane extraction or classic chloroform-methanol isolation (Bligh, Dyer 1959).

While tobacco (*Nicotiana tabacum* and other species from the *Nicotiana* genus) is the subject of examples above, other plants can be modified according to the teachings of the disclosure encompassed herein with the same technology based on their high biomass production and/or ability to accumulate oil, as discussed herein.

All patents and literature referenced herein are hereby incorporated herein in their entireties.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one". The term "about" as used herein refers to a value that is +/−10% of the value to which it refers, unless otherwise defined in any particular embodiment or example. By way of a non-limiting example, the term "about 50% water" refers to an amount of water ranging from 45% to 55%.

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

What is claimed is:

1. A gene expression cassette which enhances content of biofuel synthesis precursors in plant biomass, as compared to unmodified plants not comprising said cassette, wherein the gene expression cassette comprises: a) at least one plant expressible transcription regulating nucleotide sequence, wherein the transcription regulating nucleotide sequence is: i) a constitutive promoter; ii) an inducible promoter; iii) a tissue-specific promoter; iv) a developmentally regulated promoter; v) a nucleotide sequence which is the complement or reverse complement of any of the previously mentioned nucleotide sequences under i) to iv), and functionally linked thereto; or vi) a combination thereof; and b) a gene encoding sucrose isomerase (SI) comprising SEQ ID NO: 1, wherein the transcription regulating nucleotide sequence and the gene encoding sucrose isomerase are operably linked.

2. The gene expression cassette of claim 1, wherein the inducible promoter is selected from a tetracycline-inducible promoter, an ethanol-inducible promoter, and a hormone-inducible promoter.

3. The gene expression cassette of claim 1, wherein the transcription regulating nucleotide sequence is a promoter selected from the group consisting of a CaMV 35S, Rubisco, histone, ubiquitin, cryptic tCUP, VR-ACS1, CsVMV, ScBV, eLF4A-10, and ibAGP1 gene promoter.

4. The gene expression cassette of claim 1, wherein the gene expression cassette comprises at least one gene that, when expressed, enhances sugar production of the plant biomass.

5. The gene expression cassette of claim 1, wherein the gene expression cassette comprises at least one gene that, when expressed, enhances sugar content of the plant biomass.

6. The gene expression cassette of claim 1, wherein the gene expression cassette comprises at least one gene that, when expressed, enhances sugar production and/or storage of the plant biomass, thereby enhancing oil content of the plant biomass.

7. The gene expression cassette of claim 1, wherein the gene expression cassette comprises at least one gene that, when expressed, comprises at least one vacuole-targeting sequence.

8. The gene expression cassette of claim 1, wherein the expression of said at least one sugar enhancing gene optionally coincides with the expression of introduced or native lipid biosynthesis genes.

9. The gene expression cassette of claim 1, further comprising at least one additional gene encoding a protein selected from the group consisting of an esterase, a thioesterase, lauryl-acyl carrier protein thioesterase, acyl CoA: diacylglycerol acyltransferase, Sn-2 acyltransferase, Lec2, oleosin, and combinations thereof.

10. The gene expression cassette of claim 1, wherein the concerted expression of the transcription regulating nucleotide sequence and the at least one gene leads to elevated accumulation of fermentable sugar and lipid in modified plant biomass compared to unmodified plants.

11. A vector comprising the expression cassette of any one of claims 1-10.

12. A genetically modified plant with enhanced content of biofuel synthesis precursors in plant biomass, as compared to unmodified plants, the genetically modified plant comprising a gene expression cassette, wherein the gene expression cassette comprises: a) at least one plant expressible transcription regulating nucleotide sequence, wherein the transcription regulating nucleotide sequence is: i) a constitutive promoter; ii) an inducible promoter; iii) a tissue-specific promoter; iv) a developmentally regulated promoter; v) a nucleotide sequence which is the complement or reverse complement of any of the previously mentioned nucleotide sequences under i) to iv), and functionally linked thereto; or vi) a combination thereof; and b) a gene encoding sucrose isomerase (SI) comprising SEQ ID NO: 1, wherein the transcription regulating nucleotide sequence and the gene encoding sucrose isomerase are operably linked.

13. The genetically modified plant of claim 12, wherein said at least one gene expresses a polypeptide that enhances the content of sugars.

14. The genetically modified plant of claim 12, comprising at least one sugar- and/or lipid enhancing gene.

15. The genetically modified plant of claim 12, comprising at least one sugar enhancing gene.

16. The genetically modified plant of claim 12, wherein expression of sugar enhancing genes optionally coincides with the expression of introduced or native lipid biosynthetic genes.

17. The genetically modified plant of claim 12, wherein the expression of the transcription regulating nucleotide sequence and the at least one gene leads to elevated accumulation of fermentable sugar and/or lipid in modified plant biomass compared to unmodified plants.

18. A feedstock for production of ethanol and/or biodiesel fuels, the feedstock comprising the genetically modified plant of claim 12.

19. The genetically modified plant of claim 12, comprising at least one SI and at least one starch-degrading enzyme.

20. The genetically modified plant of claim 12, comprising at least one gene, the expression of which alters the metabolic flow in the plant as compared to unmodified plants, resulting in the accumulation of higher yield of sugar and lipid.

21. A transgenic plant product, propagation material, cells, organs, parts, calli, cell cultures, or seeds of transgenic progeny of the genetically modified plant of claim 12, each comprising said gene expression cassette.

22. The genetically modified plant according to claim 12, wherein said genetically modified plant is selected from the group consisting of monocots, dicots, tobacco, maize, pea, canola, Indian mustard, millet, sunflower, hemp, switchgrass, duckweed, sugarcane, *sorghum*, and sugar beet.

23. The genetically modified plant according to claim 12, wherein said genetically modified plant is selected from the group consisting of tobacco, hemp, switchgrass, and duckweed.

24. A genetically modified plant having an increased amount of sugar as compared to a non-genetically modified plant, and wherein said genetically modified plant comprises the gene expression cassette of claim 1.

25. A genetically modified plant having an increased amount of biofuel synthesis precursors as compared to a non-genetically modified plant, and wherein said genetically modified plant comprises the gene expression cassette of claim 1.

26. A process of engineering high-biofuel plant biomass using genetically modified plants with elevated content of biofuel synthesis precursors, compared to unmodified plants, as a host plant for metabolic engineering of lipids, comprising: a) introducing into the plant the gene expression cassette of claim 1; and b) selecting transgenic plants with elevated content of biofuel synthesis precursors.

27. A process of producing a genetically modified plant with enhanced sugar content as compared to a corresponding control plant, wherein the method comprises the steps of: a) introducing into the plant the gene expression cassette of claim 1; and b) selecting transgenic plants with enhanced sugar content.

28. The process of claim 26, wherein said biofuel synthesis precursors are sugars.

29. The process of claim 27, wherein said expression of sugar enhancing genes optionally coincides with the expression of introduced or native lipid biosynthesis genes.

30. The process of claim 27, further comprising the step of: c) concerted expression of at least one sugar-enhancing gene and at least one lipid-enhancing gene, wherein the concerted expression leads to elevated accumulation of fermentable sugar and lipid in modified plant biomass compared to unmodified plants.

31. The process of claim 27, further comprising the step of: c) expression of one or more polypeptides from the gene expression cassette, wherein expression of the one or more polypeptides from the gene expression cassette enhances sugar content of the plant biomass.

32. The process of claim 27, comprising the step of: c) expression of one or more polypeptides from the gene expression cassette, wherein expression of the one or more polypeptides from the gene expression cassette enhances sugar production of the plant biomass, and optionally, enhances oil content of the plant biomass.

33. The process of claim 27, wherein one or more of the polypeptides expressed from the gene expression cassette comprises a vacuole targeting sequence that targets the SI to plant vacuoles.

34. The process of claim 27, wherein the genetically modified plant is selected from the group consisting of monocots, dicots, tobacco, maize, pea, canola, Indian mustard, millet, sunflower, hemp, switchgrass, duckweed, sugarcane, *sorghum*, and sugar beet.

35. A method of producing biodiesel or bioethanol, the method comprising the process of claim 27, the method further comprising the step of converting the biomass of the genetically modified plant to produce biodiesel or bioethanol.

36. A process of producing biodiesel and bioethanol comprising: a) providing genetically modified plant biomass comprising the gene expression cassette of claim 1; and b) converting the plant biomass to biodiesel and bioethanol.

37. The process of claim 36, wherein said genetically modified plant biomass is selected from the group consisting of monocots, dicots, tobacco, maize, pea, canola, Indian mustard, millet, sunflower, hemp, switchgrass, duckweed, sugarcane, *sorghum*, and sugar beet.

38. A gene expression cassette which enhances content of biofuel synthesis precursors in plant biomass, as compared to unmodified plants not comprising said cassette, wherein the gene expression cassette comprises: a) at least one plant expressible transcription regulating nucleotide sequence, wherein the transcription regulating nucleotide sequence is: i) a constitutive promoter; ii) an inducible promoter; iii) a tissue-specific promoter; iv) a developmentally regulated promoter; v) a nucleotide sequence which is the complement or reverse complement of any of the previously mentioned nucleotide sequences under i) to iv), and functionally linked thereto; or vi) a combination thereof; b) a gene encoding sucrose isomerase (SI) comprising SEQ ID NO: 1; and c) at least one vacuole-targeting sequence, wherein the transcription regulating nucleotide sequence, the gene encoding sucrose isomerase, and the vacuole-targeting sequence are operably linked.

39. The gene expression cassette of claim 38, wherein the at least one vacuole-targeting sequence is selected from the group consisting of sporamin vacuolar propeptide, barley aleurone vacuolar propeptide, lectin vacuolar propeptide, tobacco chitinase vacuolar propeptide, a C-terminal propeptide of barley lectin, a C-terminal extension of tobacco chitinase A, and an N-terminal potato proteinase inhibitor vacuolar targeting sequence.

40. A process of producing a genetically modified plant with enhanced isomaltulose content as compared to a corresponding control plant, wherein the method comprises the steps of: a) introducing into the plant the gene expression cassette of claim 38; and b) selecting transgenic plants with enhanced isomaltulose content.

41. A gene expression cassette which enhances content of biofuel synthesis precursors in plant biomass, as compared to unmodified plants not comprising said cassette, wherein the gene expression cassette comprises: a) a gene encoding sucrose isomerase (SI) comprising SEQ ID NO: 1; b) at least one vacuole-targeting sequence; and c) a plant-expressible promoter operably linked to said gene encoding sucrose isomerase.

* * * * *

SEQUENCE LISTING

```
<160> NUMBER OF SEQ ID NOS: 8

<210> SEQ ID NO 1
<211> LENGTH: 1846
<212> TYPE: DNA
<213> ORGANISM: Artificial Sequence
<220> FEATURE:
<223> OTHER INFORMATION: optimized sucrose isomerase sequence

<400> SEQUENCE: 1
atggcaacac agaggagggc taacccttca tcattacatt tgattacagt tttcagttta      60
cttgtggcag tggtttctgc tagcagattc aatccaatta gactcccaac aacacatgaa     120
cctgctcctt cattaactgt gcaacagagt aatgcattgc ctacttggtg gaaacaggca     180 gtgtttatc aggtgtatcc tagaagtttt aaagatacaa atggtgatgg aattggtgat      240
ttgaacggta ttattgaaaa ccttgattat cttaaaaaac ttggaattga tgctatttgg     300
attaacccac actatgattc tccaaatact gataatggtt atgatattag agattataga     360
aagattatga aagaatatgg tactatggag gattttgata gacttatttc tgaaatgaag     420
aagaggaaca tgaggcttat gattgatatt gttattaatc acacatcaga tcaacatgca     480
tggttcgtgc agtcaaagtc tggaaaaaac aatccataca gagattacta cttttggagg     540
gatggtaaag atggtcatgc tcctaataat tatccaagtt tctttggtgg ttctgcatgg     600
gaaaaagatg ataaatcagg acaatattac ttgcattatt ttgctaagca acaaccagat     660
ttaaattggg ataatccaaa ggttagacag gatctttacg atatgttgag attttggttg     720
gataaaggtg tttctggttt aagatttgat acagttgcaa cttatagtaa aattccaaat     780
tttcctgatc tctctcaaca acagcttaaa aacttcgctg aggaatatac aaagggtcca     840
```

```
aaaattcacg attatgttaa tgaaatgaac agagaggtgc tttctcatta cgatattgct      900
acagctggtg aaattttcgg agttccactt gataaatcaa ttaagttttt cgatagaaga      960
agaaatgaat tgaatattgc atttactttc gatctcatta gattggatag agatgcagat     1020
gaaagatgga gaaggaagga ttggacttta agtcaattca gaaaaattgt tgataaggtt     1080
gatcaaacag caggagagta cggatggaat gctttctttc tcgataatca tgataaccca     1140
agggctgttt cacattttgg agatgatagg ccacagtgga gggagcatgc tgcaaaggct     1200
ttggcaactc ttactctcac tcagagagca actccattta tttaccaggg atctgagtta     1260
ggtatgacta actaccccttt taagaagatt gatgatttcg atgatgtgga agtgaaggga     1320
ttttggcaag attatgttga aacaggtaag gttaaagctg aagaatttct ccagaacgtt     1380
agacaaactt caagggataa ttcaaggaca cctttccagt gggatgcatc aaaaaatgct     1440
ggatttactt caggaacacc atggctcaaa attaacccaa attacaagga gattaattct     1500
gctgatcaga ttaataatcc taacagtgtg tttaattatt acagaaagct tattaatatt     1560
aggcatgata ttcctgcttt gacttacgga agttatattg atcttgatcc agataataat     1620
tcagtttatg catatacaag gactcttgga gcagaaaaat atctcgttgt gattaacttt     1680
aaagaagaag ttatgcatta tacattgcct ggagatttga gtattaataa agttattaca     1740
gaaataattt ctcacactat tgttaacaag aatgatagac aattgaggct tgaaccatgg     1800
caaagtggaa tttacaagct caatccttga ggagagctca gtcgac                    1846

<210> SEQ ID NO 2
<211> LENGTH: 1846
<212> TYPE: DNA
<213> ORGANISM: Artificial Sequence
<220> FEATURE:
<223> OTHER INFORMATION: optimized sucrose isomerase sequence

<400> SEQUENCE: 2
taccgttgtg tctcctcccg attgggaagt agtaatgtaa actaatgtca aaagtcaaat       60
gaacaccgtc accaaagacg atcgtctaag ttaggttaat ctgagggttg ttgtgtactt      120
ggacgaggaa gtaattgaca cgttgtctca ttacgtaacg gatgaaccac ctttgtccgt      180
cacaaaatag tccacatagg atcttcaaaa tttctatgtt taccactacc ttaaccacta      240
aacttgccat aataactttt ggaactaata gaatttttttg aaccttaact acgataaacc      300
taattgggtg tgatactaag aggtttatga ctattaccaa tactataatc tctaatatct      360
ttctaatact ttcttatacc atgatacctc ctaaaactat ctgaataaag actttacttc      420
ttctccttgt actccgaata ctaactataa caataattag tgtgtagtct agttgtacgt      480
accaagcacg tcagtttcag accttttttg ttaggtatgt ctctaatgat gaaaacctcc      540
ctaccatttc taccagtacg aggattatta ataggttcaa agaaaccacc aagacgtacc      600 cttttttctac tatttagtcc tgttataatg aacgtaataa aacgattcgt tgttggtcta      660
aatttaaccc tattaggttt ccaatctgtc ctagaaatgc tatacaactc taaaaccaac      720
ctatttccac aaagaccaaa ttctaaacta tgtcaacgtt gaatatcatt ttaaggttta      780
aaaggactag agagagttgt tgtcgaattt ttgaagcgac tccttatatg tttcccaggt      840
ttttaagtgc taatacaatt actttacttg tctctccacg aaagagtaat gctataacga      900
tgtcgaccac tttaaaagcc tcaaggtgaa ctatttagtt aattcaaaaa gctatcttct      960
tctttactta acttataacg taaatgaaag ctagagtaat ctaacctatc tctacgtcta     1020
cttctaccct cttccttcct aacctgaaat tcagttaagt cttttttaaca actattccaa     1080
```

```
ctagtttgtc gtcctctcat gcctaccttα cgaaagaaag agctattagt actattgggt    1140
tcccgacaaa gtgtaaaacc tctactatcc ggtgtcacct ccctcgtacg acgtttccga    1200
aaccgttgag aatgagagtg agtctctcgt tgaggtaaat aaatggtccc tagactcaat    1260
ccatactgat tgatgggaaa attcttctaa ctactaaagc tactcacct tcacttccct    1320 aaaaccgttc taatacaact ttgtccattc caatttcgac ttcttaaaga ggtcttgcaa    1380
tctgtttgaa gttccctatt aagttcctgt ggaaaggtca ccctacgtag ttttttacga    1440
cctaaatgaa gtccttgtgg taccgagttt taattgggtt taatgttcct ctaattaaga    1500
cgactagtct aattattagg attgtcacac aaattaataa tgtctttcga ataattataa    1560
tccgtactat aaggacgaaa ctgaatgcct tcaatataac tagaactagg tctattatta    1620
agtcaaatac gtatatgttc ctgagaacct cgtctttta tagagcaaca ctaattgaaa    1680
tttcttcttc aatacgtaat atgtaacgga cctctaaact cataattatt tcaataatgt    1740 ctttattaa gagtgtgata acaattgttc ttactatctg ttaactccga acttggtacc    1800
gtttcacctt aaatgttcga gttaggaact cctctcgagt cagctg    1846
```

```
<210> SEQ ID NO 3
<211> LENGTH: 609
<212> TYPE: PRT
<213> ORGANISM: Artificial Sequence
<220> FEATURE:
<223> OTHER INFORMATION: optimized sucrose isomerase sequence

<400> SEQUENCE: 3

Met Ala Thr Gln Arg Arg Ala Asn Pro Ser Ser Leu His Leu Ile Thr
1               5                   10                  15

Val Phe Ser Leu Leu Val Ala Val Val Ser Ala Ser Arg Phe Asn Pro
            20                  25                  30

Ile Arg Leu Pro Thr Thr His Glu Pro Ala Pro Ser Leu Thr Val Gln
        35                  40                  45

Gln Ser Asn Ala Leu Pro Thr Trp Trp Lys Gln Ala Val Phe Tyr Gln
    50                  55                  60

Val Tyr Pro Arg Ser Phe Lys Asp Thr Asn Gly Asp Gly Ile Gly Asp
65                  70                  75                  80

Leu Asn Gly Ile Ile Glu Asn Leu Asp Tyr Leu Lys Lys Leu Gly Ile
                85                  90                  95

Asp Ala Ile Trp Ile Asn Pro His Tyr Asp Ser Pro Asn Thr Asp Asn
            100                 105                 110

Gly Tyr Asp Ile Arg Asp Tyr Arg Lys Ile Met Lys Glu Tyr Gly Thr
        115                 120                 125

Met Glu Asp Phe Asp Arg Leu Ile Ser Glu Met Lys Lys Arg Asn Met
    130                 135                 140

Arg Leu Met Ile Asp Ile Val Ile Asn His Thr Ser Asp Gln His Ala
145                 150                 155                 160

Trp Phe Val Gln Ser Lys Ser Gly Lys Asn Asn Pro Tyr Arg Asp Tyr
                165                 170                 175

Tyr Phe Trp Arg Asp Gly Lys Asp Gly His Ala Pro Asn Asn Tyr Pro
            180                 185                 190

Ser Phe Phe Gly Gly Ser Ala Trp Glu Lys Asp Asp Lys Ser Gly Gln
        195                 200                 205

Tyr Tyr Leu His Tyr Phe Ala Lys Gln Gln Pro Asp Leu Asn Trp Asp
    210                 215                 220
```

```
Asn Pro Lys Val Arg Gln Asp Leu Tyr Asp Met Leu Arg Phe Trp Leu
225                 230                 235                 240

Asp Lys Gly Val Ser Gly Leu Arg Phe Asp Thr Val Ala Thr Tyr Ser
            245                 250                 255

Lys Ile Pro Asn Phe Pro Asp Leu Ser Gln Gln Leu Lys Asn Phe
        260                 265                 270

Ala Glu Glu Tyr Thr Lys Gly Pro Lys Ile His Asp Tyr Val Asn Glu
    275                 280                 285

Met Asn Arg Glu Val Leu Ser His Tyr Asp Ile Ala Thr Ala Gly Glu
    290                 295                 300

Ile Phe Gly Val Pro Leu Asp Lys Ser Ile Lys Phe Phe Asp Arg Arg
305                 310                 315                 320

Arg Asn Glu Leu Asn Ile Ala Phe Thr Phe Asp Leu Ile Arg Leu Asp
                325                 330                 335

Arg Asp Ala Asp Glu Arg Trp Arg Arg Lys Asp Trp Thr Leu Ser Gln
            340                 345                 350

Phe Arg Lys Ile Val Asp Lys Val Asp Gln Thr Ala Gly Glu Tyr Gly
        355                 360                 365

Trp Asn Ala Phe Phe Leu Asp Asn His Asp Asn Pro Arg Ala Val Ser
370                 375                 380

His Phe Gly Asp Asp Arg Pro Gln Trp Arg Glu His Ala Ala Lys Ala
385                 390                 395                 400

Leu Ala Thr Leu Thr Leu Thr Gln Arg Ala Thr Pro Phe Ile Tyr Gln
                405                 410                 415

Gly Ser Glu Leu Gly Met Thr Asn Tyr Pro Phe Lys Lys Ile Asp Asp
            420                 425                 430

Phe Asp Asp Val Glu Val Lys Gly Phe Trp Gln Asp Tyr Val Glu Thr
        435                 440                 445

Gly Lys Val Lys Ala Glu Glu Phe Leu Gln Asn Val Arg Gln Thr Ser
    450                 455                 460

Arg Asp Asn Ser Arg Thr Pro Phe Gln Trp Asp Ala Ser Lys Asn Ala
465                 470                 475                 480

Gly Phe Thr Ser Gly Thr Pro Trp Leu Lys Ile Asn Pro Asn Tyr Lys
                485                 490                 495

Glu Ile Asn Ser Ala Asp Gln Ile Asn Asn Pro Asn Ser Val Phe Asn
            500                 505                 510

Tyr Tyr Arg Lys Leu Ile Asn Ile Arg His Asp Ile Pro Ala Leu Thr
        515                 520                 525

Tyr Gly Ser Tyr Ile Asp Leu Asp Pro Asp Asn Asn Ser Val Tyr Ala
    530                 535                 540

Tyr Thr Arg Thr Leu Gly Ala Glu Lys Tyr Leu Val Val Ile Asn Phe
545                 550                 555                 560

Lys Glu Glu Val Met His Tyr Thr Leu Pro Gly Asp Leu Ser Ile Asn
                565                 570                 575

Lys Val Ile Thr Glu Asn Asn Ser His Thr Ile Val Asn Lys Asn Asp
            580                 585                 590

Arg Gln Leu Arg Leu Glu Pro Trp Gln Ser Gly Ile Tyr Lys Leu Asn
        595                 600                 605

Pro

<210> SEQ ID NO 4
<211> LENGTH: 31
<212> TYPE: DNA
<213> ORGANISM: Artificial Sequence
```

<220> FEATURE:
<223> OTHER INFORMATION: forward primer

<400> SEQUENCE: 4
ctgctagcag attcaatcca attagactcc c                              31

<210> SEQ ID NO 5
<211> LENGTH: 31
<212> TYPE: DNA
<213> ORGANISM: Artificial Sequence
<220> FEATURE:
<223> OTHER INFORMATION: reverse primer

<400> SEQUENCE: 5
taaagatcct gtctaacctt tggattatcc c                              31

<210> SEQ ID NO 6
<211> LENGTH: 1320
<212> TYPE: DNA
<213> ORGANISM: Artificial Sequence
<220> FEATURE:
<223> OTHER INFORMATION: Codon-optimized sucrose-isomerase (palatinose)
      gene sequence with signal peptides

<400> SEQUENCE: 6
atggcaacac agaggagggc taaccccttca tcattacatt tgattacagt tttcagttta      60
taccgttgtg tctcctcccg attgggaagt agtaatgtaa actaatgtca aaagtcaaat     120
cttgtggcag tggtttctgc tagcagattc aatccaatta gactcccaac aacacatgaa     180
gaacaccgtc accaaagacg atcgtctaag ttaggttaat ctgagggttg ttgtgtactt     240
cctgctcctt cattaactgt gcaacagagt aatgcattgc ctacttggtg gaaacaggca     300
ggacgaggaa gtaattgaca cgttgtctca ttacgtaacg gatgaaccac ctttgtccgt     360
gtgttttatc aggtgtatcc tagaagtttt aaagatacaa atggtgatgg aattggtgat     420
cacaaaatag tccacatagg atcttcaaaa tttctatgtt taccactacc ttaaccacta     480
ttgaacggta ttattgaaaa ccttgattat cttaaaaaac ttggaattga tgctatttgg     540
aacttgccat ataactttt ggaactaata gaatttttg aaccttaact acgataaacc     600
attaacccac actatgattc tccaaatact gataatggtt atgatattag agattataga     660
taattgggtg tgatactaag aggtttatga ctattaccaa tactataatc tctaatatct     720
aagattatga agaatatgg tactatggag gattttgata gacttatttc tgaaatgaag     780
ttctaatact ttcttatacc atgataccctc ctaaaactat ctgaataaag actttacttc     840
aagaggaaca tgaggcttat gattgatatt gttattaatc acacatcaga tcaacatgca     900
ttctccttgt actccgaata ctaactataa caataattag tgtgtagtct agttgtacgt     960
tggttcgtgc agtcaaagtc tggaaaaaac aatccataca gagattacta cttttggagg    1020
accaagcacg tcagtttcag accttttttg ttaggtatgt ctctaatgat gaaaacctcc    1080
gatggtaaag atggtcatgc tcctaataat tatccaagtt tctttggtgg ttctgcatgg    1140
ctaccatttc taccagtacg aggattatta ataggttcaa agaaaccacc aagacgtacc    1200
gaaaaagatg ataaatcagg acaatattac ttgcattatt ttgctaagca acaaccagat    1260 cttttttctac tatttagtcc tgttataatg aacgtaataa aacgattcgt tgttggtcta    1320

<210> SEQ ID NO 7
<211> LENGTH: 1560
<212> TYPE: DNA
<213> ORGANISM: Artificial Sequence
<220> FEATURE:
<223> OTHER INFORMATION: codon-optimized sucrose-isomerase
      (isomaltulose) gene sequence

<400> SEQUENCE: 7

```
ttaaattggg ataatccaaa ggttagacag gatctttacg atatgttgag attttggttg    60
aatttaaccc tattaggttt ccaatctgtc ctagaaatgc tatacaactc taaaaccaac   120
gataaaggtg tttctggttt aagatttgat acagttgcaa cttatagtaa aattccaaat   180
ctatttccac aaagaccaaa ttctaaacta tgtcaacgtt gaatatcatt ttaaggttta   240
tttcctgatc tctctcaaca acagcttaaa aacttcgctg aggaatatac aaagggtcca   300
aaaggactag agagagttgt tgtcgaattt ttgaagcgac tccttatatg tttcccaggt   360
aaaattcacg attatgttaa tgaaatgaac agagaggtgc tttctcatta cgatattgct   420
ttttaagtgc taatacaatt actttacttg tctctccacg aaagagtaat gctataacga   480
acagctggtg aaattttcgg agttccactt gataaatcaa ttaagttttt cgatagaaga   540
tgtcgaccac tttaaaagcc tcaaggtgaa ctatttagtt aattcaaaaa gctatcttct   600
agaaatgaat tgaatattgc atttactttc gatctcatta gattggatag agatgcagat   660
tctttactta actataacg taaatgaaag ctagagtaat ctaacctatc tctacgtcta   720
gaaagatgga gaaggaagga ttggacttta agtcaattca gaaaaattgt tgataaggtt   780
cttctacct cttccttcct aacctgaaat tcagttaagt cttttttaaca actattccaa   840
gatcaaacag caggagagta cggatggaat gctttctttc tcgataatca tgataaccca   900
ctagtttgtc gtcctctcat gcctacctta cgaaagaaag agctattagt actattgggt   960
agggctgttt cacattttgg agatgatagg ccacagtgga gggagcatgc tgcaaaggct  1020
tcccgacaaa gtgtaaaacc tctactatcc ggtgtcacct ccctcgtacg acgtttccga  1080
ttggcaactc ttactctcac tcagagagca actccattta tttaccaggg atctgagtta  1140
aaccgttgag aatgagagtg agtctctcgt tgaggtaaat aaatggtccc tagactcaat  1200
ggtatgacta actacccttt taagaagatt gatgatttcg atgatgtgga agtgaaggga  1260
ccatactgat tgatgggaaa attcttctaa ctactaaagc tactacacct tcacttccct  1320
ttttggcaag attatgttga aacaggtaag gttaaagctg aagaatttct ccagaacgtt  1380
aaaaccgttc taatacaact ttgtccattc caatttcgac ttcttaaaga ggtcttgcaa  1440
agacaaactt caagggataa ttcaaggaca cctttccagt gggatgcatc aaaaaatgct  1500
tctgtttgaa gttccctatt aagttcctgt ggaaaggtca ccctacgtag tttttttacga  1560
```

<210> SEQ ID NO 8
<211> LENGTH: 812
<212> TYPE: DNA
<213> ORGANISM: Artificial Sequence
<220> FEATURE:
<223> OTHER INFORMATION: codon-optimized sucrose-isomerase
      (isomaltulose) gene sequence

<400> SEQUENCE: 8

```
ggatttactt caggaacacc atggctcaaa attaacccaa attacaagga gattaattct    60
cctaaatgaa gtccttgtgg taccgagttt taattgggtt taatgttcct ctaattaaga   120
gctgatcaga ttaataatcc taacagtgtg tttaattatt acagaaagct tattaatatt   180
cgactagtct aattattagg attgtcacac aaattaataa tgtctttcga ataattaaa    240
aggcatgata ttcctgcttt gacttacgga agttatattg atcttgatcc agataataat   300
```

```
tccgtactat aaggacgaaa ctgaatgcct tcaatataac tagaactagg tctattatta      360
tcagtttatg catatacaag gactcttgga gcagaaaaat atctcgttgt gattaacttt      420
agtcaaatac gtatatgttc ctgagaacct cgtcttttta tagagcaaca ctaattgaaa      480
aaagaagaag ttatgcatta tacattgcct ggagatttga gtattaataa agttattaca      540
tttcttcttc aatacgtaat atgtaacgga cctctaaact cataattatt tcaataatgt      600
gaaaataatt ctcacactat tgttaacaag aatgatagac aattgaggct tgaaccatgg      660
cttttattaa gagtgtgata acaattgttc ttactatctg ttaactccga acttggtacc      720
caaagtggaa tttacaagct caatccttga ggagagctca gtcgacgttt caccttaaat      780
gttcgagtta ggaactcctc tcgagtcagc tg                                    812
```